United States Patent
Nigg et al.

(10) Patent No.: US 11,421,903 B2
(45) Date of Patent: Aug. 23, 2022

(54) SYSTEM AND METHOD FOR LOCAL MANAGEMENT OF BUILDING AIR QUALITY ASSURANCE

(71) Applicant: Integrated Energy Services Corporation, New York, NY (US)

(72) Inventors: Brock L. Nigg, Darien, CT (US); Steve Schlanger, Flagstaff, AZ (US); Frank Ableson, Stanhope, NJ (US)

(73) Assignee: Integrated Energy Services Corporation, New York, NY (US)

( * ) Notice: Subject to any disclaimer, the term of this patent is extended or adjusted under 35 U.S.C. 154(b) by 0 days.

(21) Appl. No.: 17/015,892

(22) Filed: Sep. 9, 2020

(65) Prior Publication Data

US 2021/0071893 A1    Mar. 11, 2021

Related U.S. Application Data

(60) Provisional application No. 62/898,248, filed on Sep. 10, 2019.

(51) Int. Cl.
*F24F 11/46* (2018.01)
*F24F 11/52* (2018.01)
(Continued)

(52) U.S. Cl.
CPC .............. *F24F 11/46* (2018.01); *F24F 11/39* (2018.01); *F24F 11/47* (2018.01); *F24F 11/52* (2018.01);
(Continued)

(58) Field of Classification Search
CPC .. F24F 11/46; F24F 11/39; F24F 11/47; F24F 11/58; F24F 11/52; F24F 11/63;
(Continued)

(56) References Cited

U.S. PATENT DOCUMENTS 7,599,815 B2    10/2009    Reichel et al.
8,428,909 B2    4/2013    Collins
(Continued)

FOREIGN PATENT DOCUMENTS

CN    109028510 A    12/2018
RU    2439442 C1    1/2012

OTHER PUBLICATIONS

International Search Report and Written Opinion of International Searching Authority for PCT/US2020/049934, ISA/RU, Moscow, Russia, dated Nov. 11, 2020.
(Continued)

*Primary Examiner* — Adnan Aziz
(74) *Attorney, Agent, or Firm* — M&B IP Analysts, LLC

(57) ABSTRACT

A bridge device operable in an air-quality control system is provided. The bridge device is connected to a plurality of sensor devices and includes a radio circuit configured to wirelessly communicate with the plurality of sensor devices over a wireless medium using an air-quality communication protocol; a transceiver configured to communicate with a remote server; a processing circuitry; a memory, the memory containing instructions that, when executed by the processing circuitry, configure the bridge device to: periodically discover the plurality of sensor devices connected to the bridge device; query each of the discovered senor devices to read at least one senor reading provided by each sensor device, the at least one senor reading is of at least an air-quality level in a vicinity of the sensor device; encapsulate the sensor readings from the plurality of sensor devices into a data frame; and send the data frame to the remote server.

21 Claims, 12 Drawing Sheets

(51) Int. Cl.
*F24F 11/58* (2018.01)
*F24F 11/63* (2018.01)
*G01N 33/00* (2006.01)
*H04W 52/02* (2009.01)
*F24F 11/39* (2018.01)
*F24F 11/47* (2018.01)
*G08C 17/02* (2006.01)
*F24F 110/50* (2018.01)
*F24F 110/20* (2018.01)
*F24F 140/60* (2018.01)
*F24F 110/70* (2018.01)
*F24F 110/74* (2018.01)
*F24F 110/40* (2018.01)
*F24F 110/66* (2018.01)
*F24F 110/10* (2018.01)

(52) U.S. Cl.
CPC ............ *F24F 11/58* (2018.01); *F24F 11/63* (2018.01); *G01N 33/0006* (2013.01); *G01N 33/0073* (2013.01); *G01N 33/0075* (2013.01); *G08C 17/02* (2013.01); *H04W 52/0206* (2013.01); *H04W 52/0235* (2013.01); *F24F 2110/10* (2018.01); *F24F 2110/20* (2018.01); *F24F 2110/40* (2018.01); *F24F 2110/50* (2018.01); *F24F 2110/66* (2018.01); *F24F 2110/70* (2018.01); *F24F 2110/74* (2018.01); *F24F 2140/60* (2018.01); *G08C 2201/12* (2013.01); *G08C 2201/40* (2013.01)

(58) Field of Classification Search
CPC ............ F24F 2110/20; F24F 2140/60; F24F 2110/70; F24F 2110/74; F24F 2110/40; F24F 2110/66; F24F 2110/10; F24F 2110/50; H04W 52/0206; H04W 52/0235; G08C 17/02; G08C 2201/12; G08C 2201/40; G01N 33/0073; G01N 33/0075
See application file for complete search history.

(56) References Cited

U.S. PATENT DOCUMENTS

| | | | |
|---|---|---|---|
| 8,682,937 B2 | 3/2014 | Ludwig | |
| 9,756,403 B2* | 9/2017 | Proud | A61B 5/02055 |
| 10,687,231 B1* | 6/2020 | Stamatakis | F24F 11/30 |
| 2003/0145644 A1* | 8/2003 | Rabbett | G01N 27/4163 73/1.06 |
| 2007/0242688 A1 | 10/2007 | McFarland | |
| 2009/0012738 A1 | 1/2009 | Hart et al. | |
| 2010/0081411 A1* | 4/2010 | Montenero | G01N 33/0075 455/404.2 |
| 2010/0177750 A1 | 7/2010 | Essinger et al. | |
| 2011/0074552 A1* | 3/2011 | Norair | G06K 7/0008 340/10.1 |
| 2012/0242453 A1* | 9/2012 | Delgado | G06K 19/0712 340/10.1 |
| 2012/0303164 A1 | 11/2012 | Smith et al. | |
| 2013/0038470 A1* | 2/2013 | Niemeyer | G01N 33/0075 340/870.11 |
| 2013/0174646 A1* | 7/2013 | Martin | G01N 33/00 73/31.02 |
| 2013/0298642 A1 | 11/2013 | Gillette, II | |
| 2014/0053586 A1 | 2/2014 | Poecher et al. | |
| 2014/0126382 A1* | 5/2014 | Tian | H04L 1/189 370/241 |
| 2014/0129004 A1 | 5/2014 | Takayama et al. | |
| 2014/0247140 A1 | 9/2014 | Proud | |
| 2015/0096352 A1 | 4/2015 | Peterson et al. | |
| 2015/0195780 A1* | 7/2015 | Liu | H04W 52/0203 370/311 |
| 2015/0285755 A1* | 10/2015 | Moss | G01N 33/0032 702/133 |
| 2016/0116181 A1 | 4/2016 | Aultman et al. | |
| 2016/0135242 A1* | 5/2016 | Hampel | H04W 76/14 370/329 |
| 2016/0360300 A1 | 12/2016 | Proud | |
| 2018/0120279 A1 | 5/2018 | Yi et al. | |
| 2018/0156484 A1* | 6/2018 | Kim | F24F 11/62 |
| 2020/0003447 A1 | 1/2020 | Lee et al. | |
| 2020/0393152 A1 | 12/2020 | Ramirez et al. | |
| 2021/0041125 A1 | 2/2021 | Liu et al. | |

OTHER PUBLICATIONS

International Search Report and Written Opinion of International Searching Authority for PCT/US2020/048472, ISA/RU, Moscow, Russia, dated Nov. 19, 2020.

International Search Report and Written Opinion of International Searching Authority for PCT/US2020/049937, ISA/RU, Moscow, Russia, dated Nov. 26, 2020.

Vaquerizo-Hdez et al., "A Low Power Consumption Algorithm for Efficient Energy Consumption in ZigBee Motes", Intelligent Systems Group, Computer Engineering Department, Universidad de Alcala; Sensors: MDPI, Aug. 19, 2017.

* cited by examiner

SYSTEM AND METHOD FOR LOCAL MANAGEMENT OF BUILDING AIR QUALITY ASSURANCE

CROSS-REFERENCE TO RELATED APPLICATIONS

This application claims the benefit of U.S. Provisional Application No. 62/898,248 filed on Sep. 10, 2019, the contents of which are hereby incorporated by reference.

TECHNICAL FIELD

The present disclosure relates generally to air quality assurance and energy management and, more particularly, to systems and methods for local management of devices for environmental monitoring, advisement and control of commercial and industrial buildings.

BACKGROUND

While certain improvements in building materials, construction techniques, and electronic systems provide for improved efficiency in operation of a building, energy costs remain among a building operator's greatest expense. Energy costs, such as those costs arising from heating or cooling a building, may vary greatly based on factors such as resident or tenant environmental preferences, demand-based energy pricing, environmental conditions, and the like. Further, building operators may wish to account for the assurance of air quality, comfort, wellness, and the like, of tenants and residents, including by assuring consistent air quality, in addition to cost-optimization, creating a complex balance of energy costs and building requirements, a balance which legacy systems may be ill-equipped to resolve.

Legacy building management systems may provide for the collection of data relating to building environmental conditions. Further, such legacy systems may include features providing for control of building conditions using devices such as thermostat-linked heating and cooling systems, remote shutoffs for conduits, and the like. While such legacy systems may provide for environmental control and data collection, legacy means may be ill-suited to high-volume data processing and may lack certain connectivity features useful in reducing operator workload and maintenance.

In addition to the inefficiencies of legacy systems in managing high-volume building data, such systems may fail to provide certain modern functionalities necessary for efficient building environmental system management. Legacy systems may lack cloud-processing systems which provide for collection and analysis of large volumes of building data. Further, legacy systems may lack the interconnectivity required to collect energy market and grid data and to respond to such data automatically. In addition, legacy systems may require manual calibration and re-calibration of sensor and regulator devices, where manual calibration and re-calibration may require a prohibitively large outlay of time and effort on the part of building management and maintenance teams.

Further, legacy systems may fail to provide for management of building wellness controls. Building wellness controls include those controls concerning health and wellness parameters of building management, such as air filter status, air quality and contamination, ventilation levels and schedules, air cleaning protocols, detection and management of chemicals and particulates, such as viruses, and the like, as opposed to comfort controls which may be directed to provision of comfortable conditions for building occupants, such as controls directed to air temperatures. Further, legacy systems may require various trade-offs between wellness, comfort, and energy efficiency in order to reach various building management goals. As a result, legacy systems may lack the capacity to provide optimized wellness, comfort, and energy solutions, requiring intensive manual adjustment of wellness, comfort, and energy parameters to reach desired building control states.

In addition to legacy building management systems, certain smaller-scale comfort and energy management systems may provide similar functionalities in smaller-scope applications, such as homes, small offices, and the like. Examples of smaller-scale comfort and energy management systems include the Nest(r) home management system by Google(r). While smaller-scale systems provide for certain energy and comfort control functionalities, such systems lack the scope of application required to provide centrally-managed control of wellness, comfort, and energy needs for larger buildings such as office towers, retail stores, and the like, as such buildings may include large numbers of management devices, complex connectivity architectures, predefined communication protocols, and the like. Further, smaller-scale systems may be primarily directed to management of comfort and energy parameters, to the exclusion of integrated safety and wellness controls. As a result, smaller-scale management systems may fail to provide functionalities and scopes of application required for use in large-scale building systems management applications.

It would therefore be advantageous to provide a solution that would overcome the challenges noted above.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "some embodiments" or "certain embodiments" may be used herein to refer to a single embodiment or multiple embodiments of the disclosure.

Certain embodiments disclosed herein include a bridge device operable in an air-quality control system, the bridge device is connected to a plurality of sensor devices, the bridge device comprising: a radio circuit configured to wirelessly communicate with the plurality of sensor devices over a wireless medium using an air-quality communication protocol; a transceiver configured to communicate with a remote server; a processing circuitry; a memory, the memory containing instructions that, when executed by the processing circuitry, configure the bridge device to: periodically discover the plurality of sensor devices connected to the bridge device; query each of the discovered senor devices to read at least one senor reading provided by each sensor device, wherein the at least one senor reading is of at least an air-quality level in a vicinity of the sensor device; encapsulate the sensor readings from the plurality of sensor devices into a data frame; and send the data frame to the remote server.

Certain embodiments disclosed herein include a method for operating a bridge device, wherein the bridge device is connected to a plurality of sensor devices in an air-quality control system. The method comprises periodically discovering the plurality of sensor devices connected to the bridge device; querying each of the discovered senor devices to read at least one sensor reading provided by each sensor device, wherein the at least one sensor reading is of at least an air-quality level in a vicinity of the sensor device; encapsulating the sensor readings from the plurality of sensor devices into a data frame; and sending the data frame to a remote server.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1:
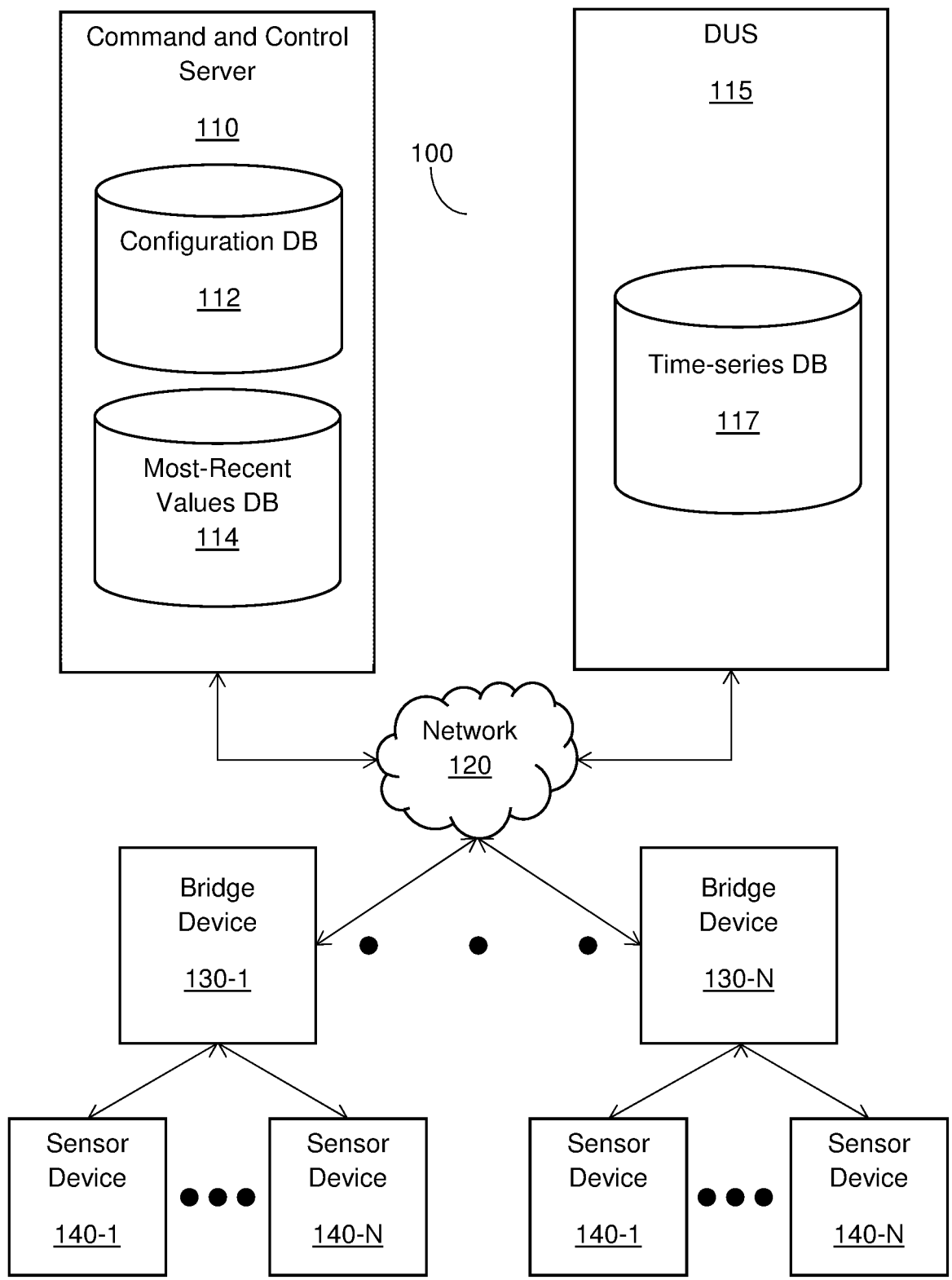
FIG. 1 is a network diagram utilized to describe a system for local management of building air quality assurance, comfort, and energy management devices, according to an embodiment.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

FIG. 1 is an example network system 100 depicting the various embodiments for local management of building air quality assurance, comfort, and energy management devices, according to an embodiment. A network system 100 may include one or more components such as, as examples and without limitation, a command and control server (CCS) 110, a data upload server (DUS) 115, a network 120, one or more bridge devices 130-1 through 130-N (hereinafter, "bridge device" 130 or "bridge devices" 130), as well as one or more sensor devices 140-1 through 140-N (hereinafter, "sensor device" 140 or "sensor devices" 140). Further, it may be understood that sensor devices 140 may include other, like, devices pertinent to the operation of a network system, as described herein, including, without limitation, devices for collection of room-level or space-level tenant or user inputs, such as adjustable thermostats, and the like, as well as any combination thereof, providing for local, integrated holistic building and space management. In an embodiment, a bridge device 130 is a building air quality assurance, comfort, or energy management device.

The CCS 110 provides for cloud-level administration of one or more bridge devices 130. The CCS 110 may include a configuration database 112, a most-recent values database 114, and the like, as well as any combination thereof. The CCS 110 may be a local system, implemented in the same physical location as various components of the network system 100, as a cloud system, implemented as a remote server, and the like, as well as any combination thereof. Further, in an embodiment, other, like, devices may be implemented to execute some or all of the functions of the CCS 110, as described herein, including, without limitation, one or more remote servers, and the like, as well as any combination thereof. The CCS 110 may be configured to communicate with one or more components of the network system 100 via the network 120, according to the means described hereinbelow. Further, the CCS 110 may be configured to execute one or more of the methods or processes described hereinbelow, including execution of various data processing methods and routines. The CCS 110 may include various processing, memory, and networking components, and the like, allowing the CCS 110 to execute instructions and provide data processing. The CCS 110 may be implemented as physical hardware, as software virtualizing physical hardware, or as a combination of physical and virtualized components. In an embodiment, the CCS 110 may be configured to operate as a data upload server (DUS) 115, as described hereinbelow.

The most recent values database 114 provides storage for register data, as may be collected according to the processes described hereinbelow, organized by order of receipt. Registers may include data features describing, variously, device and component operating systems, device-specific data features, user-defined features, and the like. Register data may include data relating to the operating system or systems of various components of a network system 100.

In addition, register data may include data relating to the operation of various components of a network system, describing component-specific data features, such as, as an example and without limitation, the firmware version of a specific sensor. Further, register data may include user register data, where user register data is data relevant to a user's custom purpose. As an example, user register data may include custom-generated instruction sets for personalizing sensor device data output formats.

The configuration database 112 provides storage for system configuration instructions and collected data. Data which may be stored in the configuration database 112 includes, as examples and without limitation, sensor calibration data, building management system interface data, updated code images, various factory commands, DUS assignments, market and environmental data, register updates, device-specific commands, other, like, data, and any combination thereof.

The data upload server (DUS) 115, is a cloud-level server providing for collection and storage of data from one or more bridge devices 130, more sensors 140-1 through 140-N (hereinafter, "sensor" 140), connected building management systems (not shown), and the like, as well as any combination thereof.

The DUS 115 may be a resident server, located and operated on-location where the one or more bridge devices 130 and sensor devices 140 are deployed. Further, the DUS 115 may be a hosted server, located off-site and, in an embodiment, hosted by a platform configured to provide cloud computing, storage, and other, like, services, including, as examples and without limitation, Amazon(r) Web Services, Microsoft(r) Azure, and other, like, platforms. The DUS 115 may include one or more storage or memory components, such as the time series database 117, and the like. The time series database 117 may be configured to store data received or collected according to the methods described hereinbelow, as well as other, like, methods. Data stored in the DUS 115, including data stored in the time series database 117, may be encrypted, unencrypted, or partially-encrypted. Further, stored data may be compressed to various degrees and may be stored to one or more physical partitions or other, like, separated storage allocations. The DUS 115, and any sub-component thereof, may be implemented as physical hardware, as software virtualizing physical hardware, or as a combination of physical and virtualized components. Further, the DUS 115 may be interconnected with the various components of the network system 100, via the network 120, according to the various means described hereinbelow.

The network 120 provides interconnectivity between the various components of the network system 100. The network 120 may be, but is not limited to, a wireless, cellular, or wired network, a local area network (LAN), a wide area network (WAN), a metro area network (MAN), the Internet, the worldwide web (WWW), similar networks, and any combination thereof. The network may be a full-physical network, including exclusively physical hardware, a fully-virtual network, including only simulated or otherwise virtualized components, or a hybrid physical-virtual network, including both physical and virtualized components. Further, the network 120 may be configured to encrypt data, both at rest and in motion, and to transmit encrypted, unencrypted, or partially-encrypted data.

The bridge devices 130 are devices configured to serve as intermediaries between the sensor devices 140 and the various components of the network system 100. The bridge devices 130 may be configured to, as examples and without limitation, collect data from various sensor devices 140, to upload or push instructions to the various sensor devices 140, to upload or push collected data to the various components of the network system 100, to collect, from the various components of the network system 100, various instructions, to collect data, independent of the various sensor devices 140, to execute instructions, and the like, as well as any combination thereof. Further, a detailed view of a bridge device 130, and an associated microcontroller, are described, respectively, with respect to FIGS. 2a and 2b, below. In addition, an example software architecture for a bridge device 130 is described with respect to FIG. 3, below. A bridge device 130 may be further configured to communicate with a CCS 110 via those means described with respect to the network 120, wherein the CCS may be configured to control the bridge device and to interface with one or more components of a building management system (BMS).

In an embodiment, a bridge device 130 may be configured to function as a building management system (BMS) controller, providing connectivity and BMS integration functionality in conjunction with a CCS 110, and various databases included in the CCS 110, as described hereinabove. According to the same embodiment, a network system 100 wherein a bridge device 130 is configured to function as a BMS controller, the respective network system 100 may be modified to omit one or more components shown in the example figure including, without limitation, the DUS 115, and the like, as well as any combination thereof. In yet another embodiment, the bridge devices 130 may be configured to connect with the various components of the network system 100 via the network 120, according to the means described hereinabove. Further, the bridge devices 130 may be configured to connect with the various sensor devices 140 via wired or wireless means, or any combination thereof, such as those described hereinabove, via those protocols described with respect to the network 120, as well as other, like, protocols, or any combination thereof. In addition, the bridge devices 130 may be configured to encrypt data, both at rest and in motion, and to transmit data with varying degrees of encryption. In an additional embodiment, the bridge device 130 may be deployed remotely from the plurality of sensor devices 140, the building management system, and the like, as well as any combination thereof.

According to the disclosed embodiments, the bridge devices 130 may be configured to execute instructions, and process data, for local management of building air quality assurance, comfort, and energy management devices. Local building air quality assurance, comfort, and energy management devices may be, sensor devices 140, other, like, devices, and any combination thereof, some or all of which may be configured to provide functionality pertaining to building energy management, building air quality and comfort, or both. The bridge devices 130 may be configured to execute instructions and process data relevant to the various components of the system via connections to the various devices according to various pre-defined communication protocols, patterns, exchange systems, and the like, including via the network, as described hereinabove. Further, the bridge device 130 may be configured to execute some or all of the processes described hereinbelow. In an embodiment, a bridge device 130 may be configured to issue one or more commands to various sensor devices 140 on one or more bases including, without limitation, synchronized protocol-defined bases, such as those relevant to the methods described hereinbelow, asynchronous bases, such as may be implemented for non-standard bridge-sensor communications, other, like, bases, and any combination thereof. In a further embodiment, commands issued by a bridge device 130 to one or more sensor devices 140 on an asynchronous basis may include, without limitation, one or more self-calibration commands pertinent to self-calibration of a sensor device 140, other, like, commands, and any combination thereof. In an additional embodiment, commands issued by a bridge device 130 to one or more sensor devices 140 on an asynchronous basis may include, without limitation, one or more commands responsive to instructions received from a CCS 110, and the like, as well as any combination thereof.

The sensors 140 are devices configured to provide for monitoring and control of building air quality, comfort, and energy management. The sensors 140 may be devices such as, as examples and without limitation, sensors, such as thermometers and gas detection and measurement sensors, building systems actuators, such as airflow control valves, and other, like, devices, as well as any combination thereof. Further, sensor devices 140 may be configured to collect data and to transmit collected data to the various components of the network system 100 via the bridge devices 130, to execute instructions received, via the bridge devices 130, from the various components of the network system 100, to execute other, like, functions, as well as any combination thereof. In addition, sensors 140 may be configured to include one or more components configured to collect user input, display information to users, or both, including, without limitation, touch screens, and the like, as well as any combination thereof. The sensor devices 140 may be configured to connect with the bridge devices 130 via those means described hereinabove.

Figure 2A:
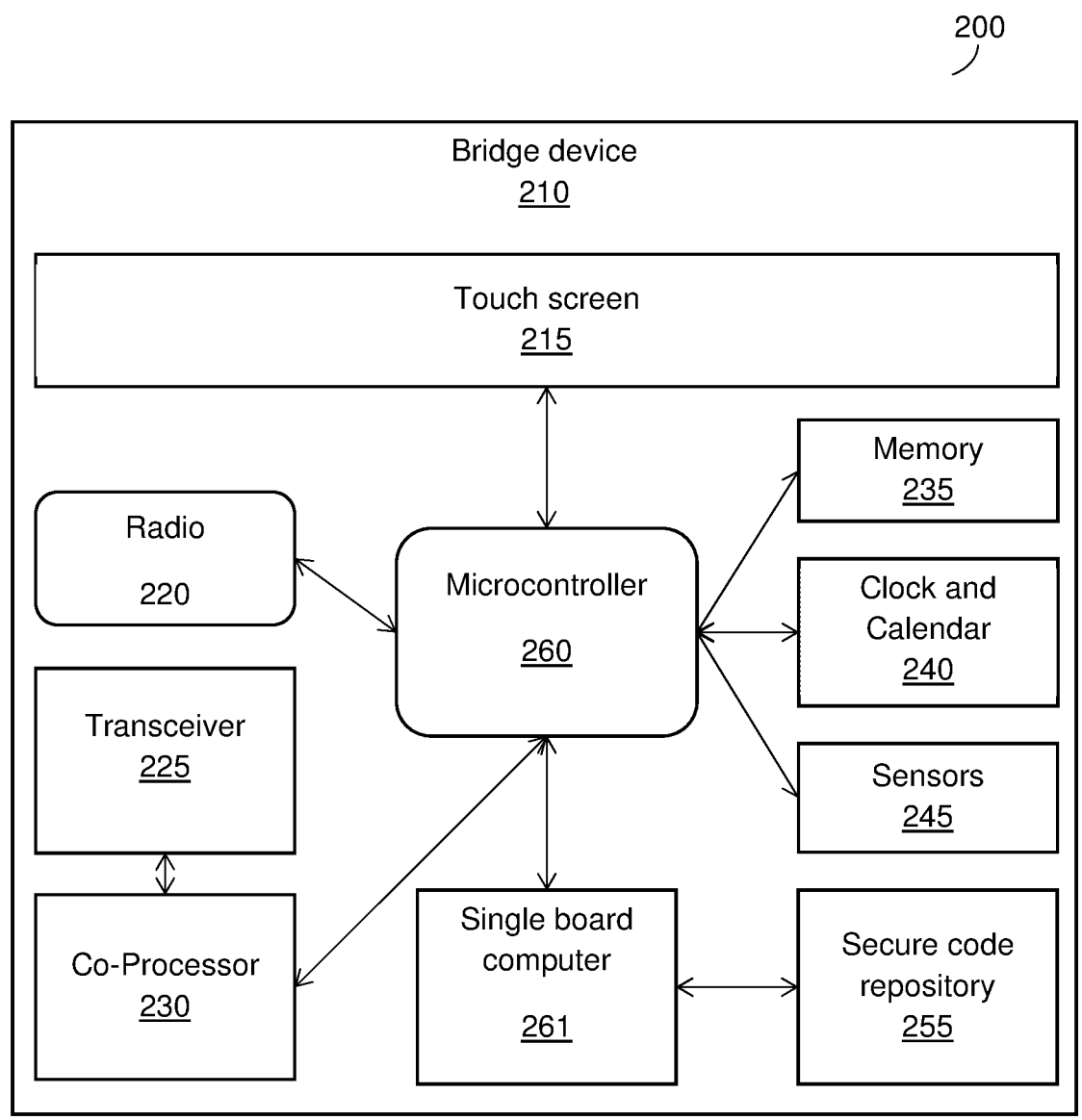
FIG. 2a is a hardware diagram depicting a bridge device for local control of building air quality assurance, comfort, and energy management devices, according to an embodiment.

FIG. 2a is an example hardware diagram depicting a bridge device 210 for a device for local control of building air quality assurance, comfort, and energy management devices, according to an embodiment. The bridge device can be realized as a hardware unit including a custom printed circuit board (PCB) utilized for the local management of building air quality assurance, comfort, and energy management devices.

In an embodiment, the bridge device 210 may include, without limitation, a screen 215, such as a touch screen, a radio 220, a transceiver 225, a Co-Processor 230, a memory 235, a clock and calendar 240, one or more sensors 245 (hereinafter referred to as "sensors" 245), a secure code repository 255, a microcontroller 260, a single-board computer (SBC) 261, other, like components, and any combination thereof.

The touch screen 215 is a touch screen configured to display text, graphics, animation, device settings, collected sensor device readings, and the like, to collect user touch inputs including, as examples and without limitation, touches, taps, swipes, and the like, as well as any combination thereof. The touch screen 215 may be configured to simultaneously display content as described and to collect one or more user inputs. The touch screen 215 may be a color display touch screen. Further, the touch screen 215 may be configured to connect to the microcontroller 260 via one or more connections including, as examples and without limitation, analog connections, serial peripheral interface (SPI), other, like, connections, and any combination thereof. The touch screen 215 may be configured to connect to the microcontroller 260 for purposes including, without limitation, sending data, receiving data, other, like, purposes, and any combination thereof.

The radio 220 is a radio circuit configured to communicate with one or more components of a network system, such as the system, 100, of FIG. 1, above, including by use of an air-quality communication. In an embodiment, an air-quality communication protocol may be configured to provide for maximization of a distance between a bridge device an a sensor device, minimization of power consumption by one or more sensor devices, and the like, as well as any combination thereof. The air-quality communication protocol is an encrypted protocol where the encryption is performed using a set of encryption keys stored locally at the bridge 210.

The radio 220 may be configured to communicate with various devices via means including, as examples and without limitation, radio-frequency (RF) communication, Wi-Fi, Bluetooth(r), industrial, scientific and medical (ISM) radio bands, cellular data, long-term evolution (LTE), and the like, as well as any combination thereof. Further, the radio 220 may be configured to communicate encrypted, unencrypted, or partially-encrypted data, including by encrypting data, both at rest and in motion. The radio 220 may be configured to communicate with one or more sensor devices, such as the sensor devices, 140, of FIG. 1, above, for purposes including, without limitation, sending data, receiving data, and the like, as well as any combination thereof. The radio 220 may be connected to the microcontroller 260 via one or more means including, without limitation, SPI connections, and the like, and any combination thereof, for purposes including, without limitation, sending and receiving data, and the like, as well as any combination thereof.

The transceiver 225 is an interface configured for communication with various components of one or more building air quality assurance, comfort, and energy management systems. The transceiver 225 may be configured to provide connection between a bridge device and various building management systems, including those operating via systems such as, as examples and without limitation, BACNet, Modbus, and the like, as well as any combination thereof. Further, the transceiver 225 may be connected with the Co-Processor 230 for purposes including, as examples and without limitation, processing data received via the transceiver 225, processing data for transmission via the transceiver 225, for other, like, purposes, and any combination thereof. The transceiver 225 may be connected to the Co-Processor 230 by various means including, without limitation, SPI connections, as may be implemented bi physical connection of component transistor-transistor logic (TTL) pins, and the like. In an embodiment, the transceiver 225 supports RS-type serial communication standards including, without limitation, RS485, RS422, RS232, and the like, As well as any combination thereof, as defined by the EIA.

The Co-Processor 230 is a data processing unit configured to analyze modify, or otherwise process data received from, and data bound for, the transceiver 225, as well as other, like, data, or any combination thereof. The Co-Processor 230 may be connected to the microcontroller 260 via one or more means including, without limitation, SPI connections, and the like, and any combination thereof, for purposes including, without limitation, sending and receiving data, and the like, as well as any combination thereof. In an embodiment, the Co-Processor 230 may include memory specific to the Co-Processor 230. Further, in an embodiment, the memory included in the Co-Processor 230 may include an update staging memory or storage feature, including data relevant to the staging of various over-the-air (OTA) updates for devices connected to the bridge device 210 via the transceiver 225.

The memory 235 is a non-volatile memory unit (e.g., EEPROM) configured to provide memory access for various operations performed by the components of the bridge device 210. The memory 235 may include one or more physical memory units. In an embodiment, the memory 235 and the secure code repository 255 may be portions or partitions of the same physical memory unit. The memory 235 may be connected to the microcontroller 260 via one or more means including, without limitation, SPI connections, and the like, and any combination thereof, for purposes including, without limitation, sending and receiving data, and the like, as well as any combination thereof.

The clock and calendar 240 are one or more components configured to persistently store current dates and times and to, as needed, provide stored dates and times to various other components of the bridge device 210. The clock and calendar 240 may be a real-time clock and calendar, capable of providing to-the-second time and date updates, as may be requested. In an embodiment, the clock and calendar 240 may include a battery, or may be otherwise connected to a battery disposed within the bridge device 210, to maintain power to the clock and calendar 240 when the bridge device 210 is unpowered. The clock and calendar 240 may be connected to the microcontroller 260 via one or more means including, without limitation, I-squared-C (I2C) connections, and the like, and any combination thereof, for purposes including, without limitation, sending and receiving data, and the like, as well as any combination thereof. Further, the clock and calendar 240 may be configured to provide a synchronized time slot for communication between the bridge device and the plurality of sensor devices.

The sensors 245 are various sensors configured to measure and collect data regarding the area surrounding the bridge device 210. Although only one unit is included in the example diagram, it may be understood that the sensors 245 may include one or more sensors, including sensors of different types, without loss of generality or departure from the scope of the disclosure. The sensors 245 may include, as examples and without limitation, temperature sensors, relative humidity sensors, light level sensors, and the like, as well as any combination thereof. The sensors 245 may be connected to the microcontroller 260 via one or more means including, without limitation, I2C connections, and the like, and any combination thereof, for purposes including, without limitation, sending and receiving data, and the like, as well as any combination thereof.

The bridge device 210 is configured with a serial number device which is a unique identification of the bridge device 210. The serial number device may be a memory chip that can encode various attributes of the bridge device 210 including, as examples and without limitation, manufacturing date, manufacturing location, lot number, batch number, and the like, as well as any combination thereof. In an embodiment, the serial number device may be re-writeable, providing for modification of the serial number of the bridge device 210. In an embodiment, the bridge device 210 serial number device or component may be the 32-bit serial number, 290 (FIG. 2b), included in the microcontroller, 260, as described with respect to FIG. 2b, below.

The secure code repository 255 is a non-volatile memory for various components of the bridge 130. The secure code repository 255 may be configured to warehouse, archive, or otherwise store code data and related resources for subsequent access. The secure code repository 255 may be further configured to store one or more instructions, commands, and the like, including, without limitation, instructions for activating the bridge device 130, instructions for collection of sensor device 140 readings, instructions for activating collection of data from a bridge device 130, and the like, as well as any combination thereof. Further, the secure code repository 255 may be secured by application of one or more techniques including, as examples and without limitation, application of password protection, application of encryption, including by encryption of data at rest and in motion by the secure code repository 255, other, like, techniques, and any combination thereof. The secure code repository 255 may be separate from, and connected to, a Secure Digital (SD) card, such as the SD card, 320, of FIG. 3, below, where an SD card may be included in an SBC 261, via one or more means including, without limitation, SPI connections, and the like, and any combination thereof, for purposes including, without limitation, sending and receiving data, and the like, as well as any combination thereof. The secure code repository 255 may be configured to store data otherwise stored on an SD card, as described hereinabove, providing for non-removeable storage of application code, metadata, and the like, as well as various combinations thereof.

The single-board computer (SBC) 261 is a computing unit, contained to a single physical component, configured to execute one or more processes, as described hereinbelow, including the execution of one or more application layers, and the various processes included therein, such as the application layer, 310, of FIG. 3, below. The application of an SBC 261 to the execution of application layer processes is described in greater detail with respect to FIG. 3, below. The SBC 261, and various components thereof, may be configured to connect to the microcontroller 260 via one or more means including, without limitation, SPI connections, and the like, as well as any combination thereof.

Further, as described hereinabove, the SBC 261, and the various components thereof, including, without limitation, the SD card, 320, of FIG. 3, below, may be configured to connect to the secure code repository 255 via one or more means including, without limitation, SPI connections, and the like, as well as any combination thereof. In addition, the SBC 261 may be configured to connect to a network, such as the network, 120, of FIG. 1, above, via one or more means including, without limitation, ethernet connections, those various connections described with respect to the network, 120, of FIG. 1, above, other, like, connections, and any combination thereof. In an embodiment, the SBC 261 may be configured to include one or more on-board storage or memory modules, providing for storage of data, such as may be generated or collected during the execution of the various processes described hereinbelow, and the like, as well as any combination thereof. In a further embodiment, the SBC 261 may be excluded from the bridge device 210, with the functionalities thereof being variously reassigned among the various components of the bridge device 210.

The microcontroller 260 is a processor, or other, like, processing circuitry, configured to execute one or more instructions, scripts, commands, and the like. The executed instructions may be similar or identical to those processes hereinbelow. The microcontroller 260 may be configured as a single physical unit, or as one or more separate, interconnected units. The microcontroller 260 may be connected to one or more bridge device application layers, such as the application layer, 310, of FIG. 3, below, via means including, without limitation, SPI connections, and the like, as well as any combination thereof. Further, the microcontroller 260 may be configured to execute code from one or more sources including, without limitation, the resident code, 331, of FIG. 3, below. The microcontroller 260 is described in detail with respect to FIG. 2b, below.

The microcontroller 260 may be realized as one or more hardware logic components and circuits. For example, and without limitation, illustrative types of hardware logic components that can be used include field programmable gate arrays (FPGAs), application-specific integrated circuits (ASICs), Application-specific standard products (ASSPs), system-on-a-chip systems (SOCs), graphics processing units (GPUs), tensor processing units (TPUs), general-purpose microprocessors, microcontrollers, digital signal processors (DSPs), and the like, or any other hardware logic components that can perform calculations or other manipulations of information.

Figure 2B:
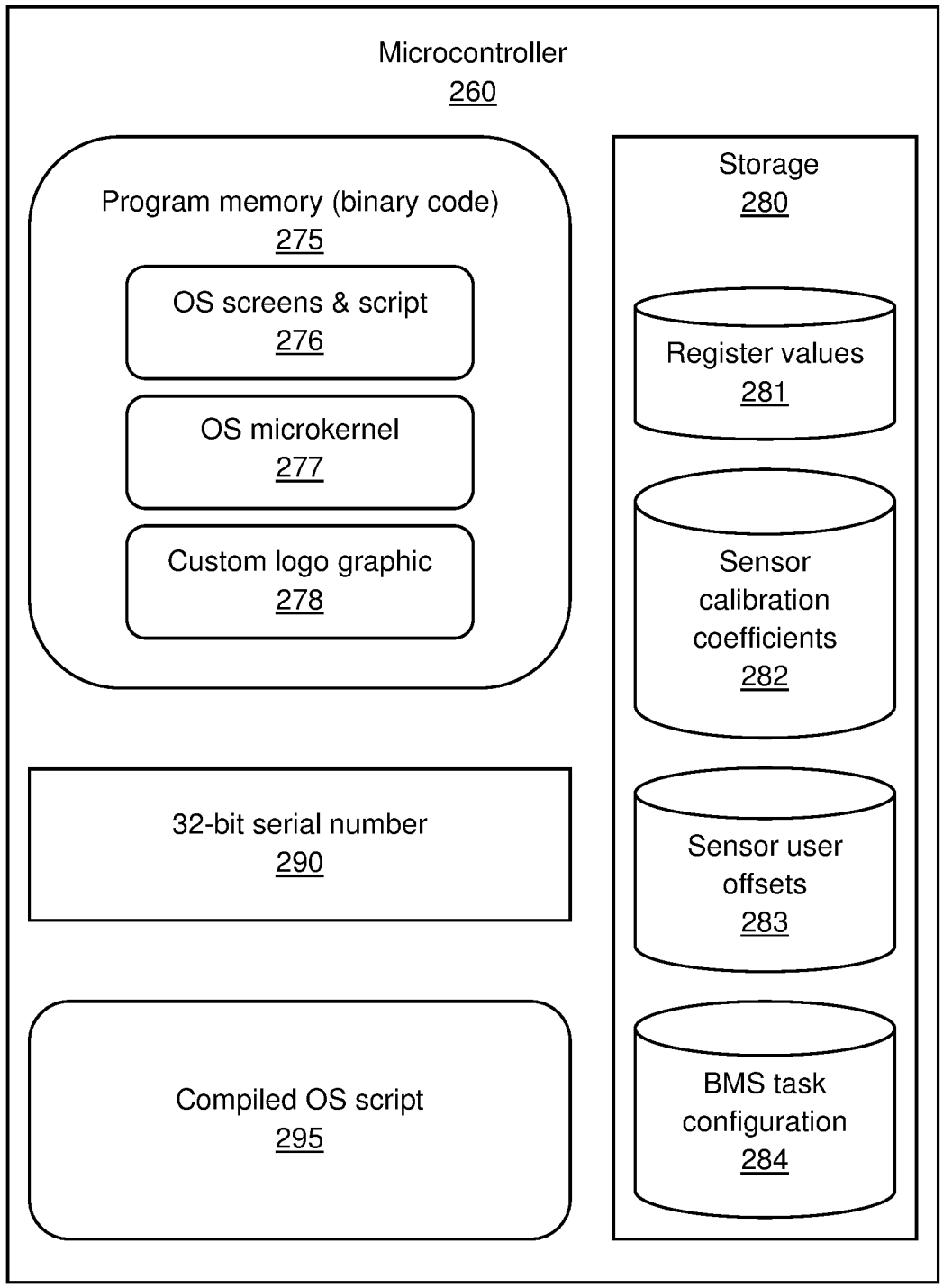
FIG. 2b is a block diagram depicting a microcontroller for a device for local control of building air quality assurance, comfort, and energy management devices, according to an embodiment.

FIG. 2b is a block diagram 265 depicting a microcontroller 260 for a device for local control of building air quality assurance, comfort, and energy management devices, according to an embodiment. The microcontroller 260 is a hardware device configured to execute one or more instructions, commands, scripts, and the like for purposes including, without limitation, local management of building air quality assurance, comfort, and energy management devices. The microcontroller 260 includes various sub-components, both physical and virtualized, as well as data features, scripts, and the like. The microcontroller 260 may include, without limitation, a program memory 275, a storage 280, a compiled operating system (OS) script 295, and the like, as well as any combination thereof.

The program memory 275 is a memory component of the microcontroller 260 including one or more binary code data features. The program memory 275 may be configured to store, temporarily, permanently, or semi-permanently, data related to various processing applications, as may be applicable to the microcontroller 260, including, without limitation, device firmware, and the like, as well as any combination thereof. The program memory 275 may include data features, in binary code format, including, as examples and without limitation, OS screens and scripts 276, pertaining to operating system display and functionality, an OS microkernel 277, relevant for running personalized code customizations, custom logo graphics 278, as may be provided by users, manufacturers, system administrators, and the like, as well as other, like, data features and any combination thereof. In an embodiment, the program memory 275 is utilized to store personalization features assures air quality, as such reducing the bridge device footprint, and size.

The storage 280 is a data storage component configured to warehouse, archive, or otherwise store data relevant to the operation of the microcontroller 260. The storage 280 may include storage of register values, as may be applicable to bridge, command and control server, and sensor device operations, storage of sensor calibration coefficients 282, as may be relevant to calibration of sensors included in bridge devices, storage of sensor user offsets 283, as may be relevant to the various sensors described above, storage of building management system (BMS) configurations, as may be applicable to BMS integration, as well as other, like, storage portions, as well as any combination thereof.

Further, in an embodiment, the storage 280 may include storage of OTA update data features, as may be relevant to various OTA update processes, including, without limitation, code binaries, scripts, logos, and the like, as well as any combination thereof. In an additional embodiment, the storage 280 may be eliminated and individual storage units may be included individually in the microcontroller 260, such as by direct connection of individual storage components to the various components of the microcontroller 260. Further, in an embodiment, the storage 280 may be the memory 235, of FIG. 2a, above.

The compiled OS script 295 includes one or more instructions, commands, or other, like, directions configured to execute one or more functions through the microcontroller 260.

Figure 3:
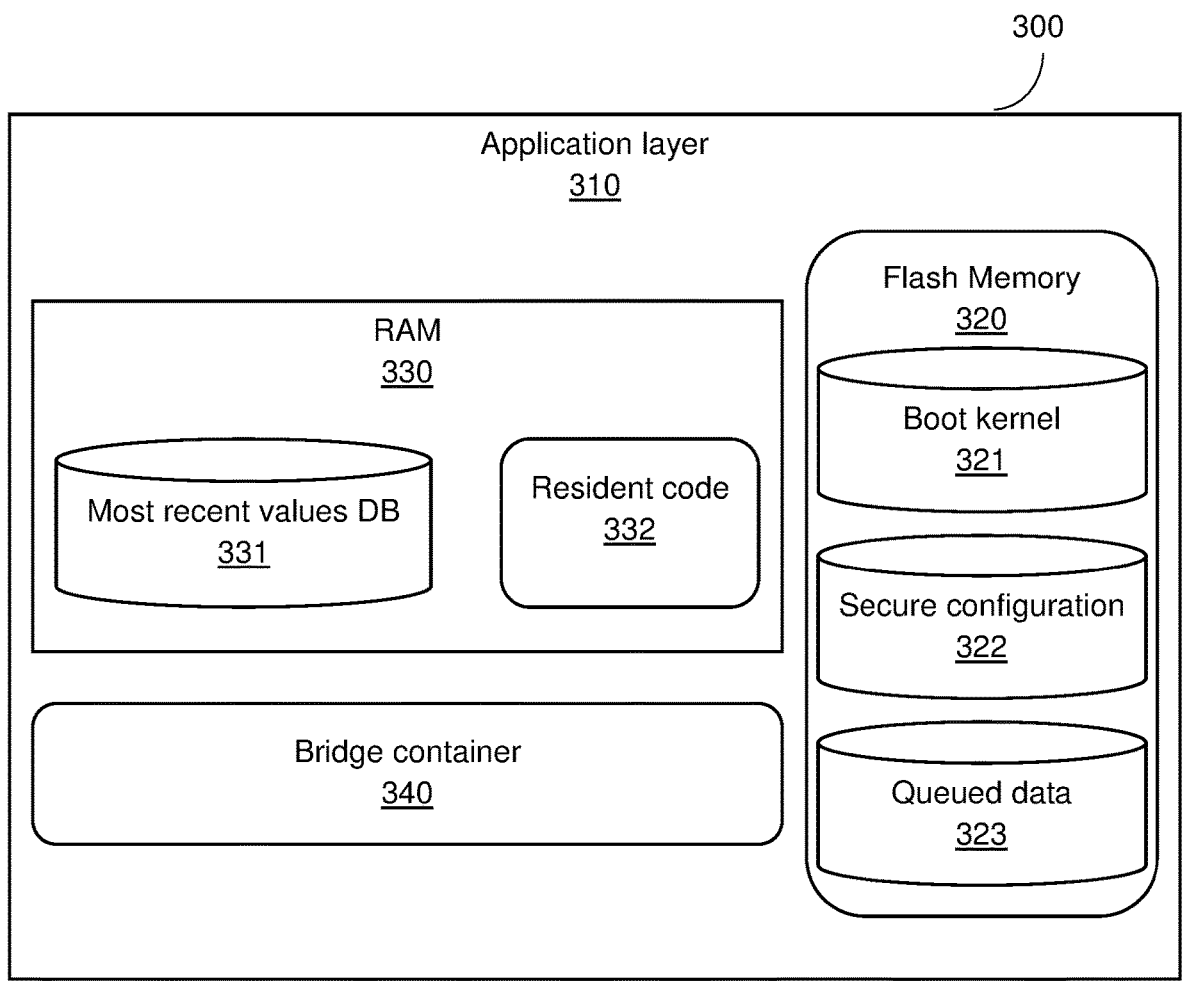
FIG. 3 is an architecture diagram depicting an architecture for local control of building air quality assurance, comfort, and energy management devices, according to an embodiment.

FIG. 3 is an example diagram depicting an architecture 300 for local control of building air quality assurance, according to an embodiment. The architecture 300 includes an application layer 310, providing for execution of one or more processes described hereinbelow. The application layer 310 further includes random-access memory (RAM) 330, a flash memory 320, and a bridge container 340. The application layer 310 may be configured to run on one or more computing hardware components such as, without limitation, the SBC, 261, of FIG. 1, above. In addition to the connectivity of the various sub-components of the application layer 310, as described herein, the application layer 310 may be configured to communicate with one or more components of a network system, such as the network system, 100, of FIG. 1, above, including a data upload server (DUS), 115, and an included time series database, 117, both of FIG. 1, above, by means including, without limitation, connection via Hypertext Transfer Protocol Secure (HTTPS), via other, like, means, and any combination thereof.

The flash memory 320 is a memory or storage component configured to provide storage for one or more data features relevant to the operation of the application layer 310 and the various components thereof. The flash memory 320 may include one or more storage portions, configured to store or otherwise retain data relevant to various aspects of the application layer. The flash memory 320 may include storage portions relevant to a bridge device boot kernel, applicable to device boot operations, a secure configuration 322, applicable to one or more pre-set or user-defined application layer 310 configurations, queued data 323, relevant to storage of data for subsequent processing or application, and the like, as well as any combination thereof.

In an embodiment, flash memory 320 may be further configured to store data relevant to the operating system of an SBC, such as the SBC, 261, of FIG. 2a, above. Further, in an embodiment, the flash memory 320 may be configured to store data collected from one or more connected devices, including, as examples and without limitation, the host bridge device, 130, of FIG. 1, above, various sensor devices, 140, of FIG. 1, above connected to the host bridge device, and the like, as well as any combination thereof, providing storage of data in the event that one or more target data upload servers (DUSs), such as the DUS, 115, of FIG. 1, above, are inaccessible. In an additional embodiment, the flash memory 320 may be configured as a removable storage medium.

The RAM 330 is memory configured to provide temporary storage for the application layer 310. The RAM 330 may be configured in write-only mode, read-only mode, or read-write mode. The RAM 330 may further include a most recent values database 331, applicable to the storage of various register values generated or collected during the operation of various processes described hereinbelow, as well as a resident code portion 332. The resident code portion 332 may be code applicable to the execution of one or more processes described hereinbelow and may be configured to connect with various components of a network system, such as the network system, 100, of FIG. 1, above, including, as an example and without limitation, with a CCS, 110, of FIG. 1, above, with other, like, components, or any combination thereof. Code included in the resident code portion 332 may be collected from one or more sources including, without limitation, the flash memory 320, the SBC, 261, the memory 235, of FIG. 2a, above, from other, like, sources, and any combination thereof. Further, where code included in the resident code portion 332 is collected from the bridge device 210 via one or more means including, without limitation, via SPI connections, via other, like, connections, and any combination thereof.

The bridge container 340 may be an isolated software instance configured to provide encapsulated functionality for the various components of the bridge device, 130, of FIG. 1, above. The bridge container 340 may be implemented as hardware, software, or any combination thereof. The bridge container 340 may be configured to connect to various components of a network system, such as the network system, 100, of FIG. 1 above, including, without limitation, a CCS, 110, of FIG. 1, above, as well as a configuration database which may be disposed therein, via means including, without limitation, communication via one or more Application Programming Interfaces (APIS), and the like, over protocols such as HTTPS, and the like, and any combination thereof.

Figure 4:
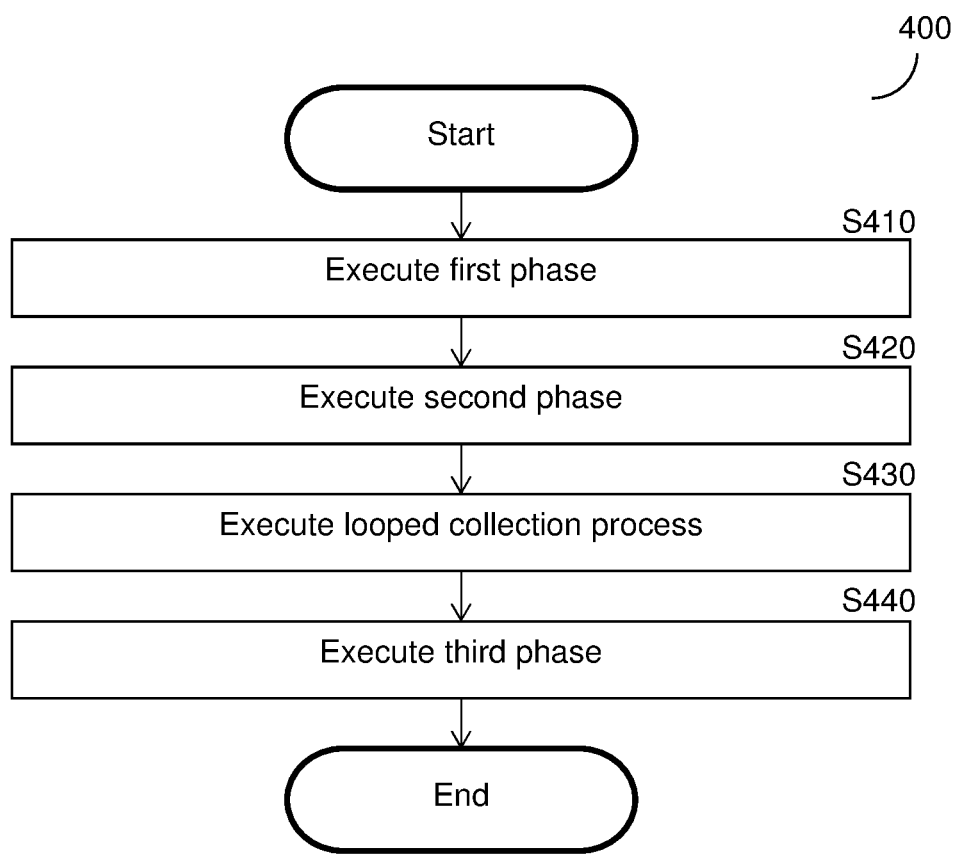
FIG. 4 is a flowchart 400 depicting a process for collecting data from one or more local devices, according to an embodiment.

FIG. 4 is a flowchart 400 depicting a process for collecting data from one or more local devices, according to an embodiment.

At S410, a first phase of a local device data collection process is executed. A first phase of a local device data collection process includes initiation of a data collection cycle, communication between a bridge device and a CCS, receipt of data and instructions, execution of selective actions, querying of a device microcontroller, transmission of data to bridge application code, and storage of received values. A detailed description of a first phase of a local device data collection process is described with respect to FIG. 5, below.

At S420, a second phase of a local device data collection process is executed. A second phase of a local device data collection process includes initiation of sensor discovery, initiation of radio frequency (RF) querying, receipt of a sensor wake-up response, passing-through RF responses, processing of sensor responses, analysis of lists of found sensors, and looping over found sensors. A second phase of a local device data collection process is described in detail with respect to FIG. 6, below.

At S430, a looped data collection process is executed. A looped data collection process includes initiation of communication querying, initiation of RF querying, receipt of query responses, storage of received values, determination of whether all devices have been queried, and initiation of a sensor sleep command. A looped data collection process is described in detail with respect to FIG. 7, below. A looped data collection process, as executed at S430, may be included as a step of a prior phase of the process described with respect to FIG. 4, and the processes described hereinbelow, including, without limitation, inclusion at S670 of FIG. 6, below.

At S440, a third phase of a local device data collection process is executed. A third phase of a local data collection process includes initiation of a low-power RF command, packaging data for upload, where packaging data for upload may include persisting data in a queue, and the like, and uploading data. A third phase of a local device data collection process is described with respect to FIG. 8, below.

Figure 5:
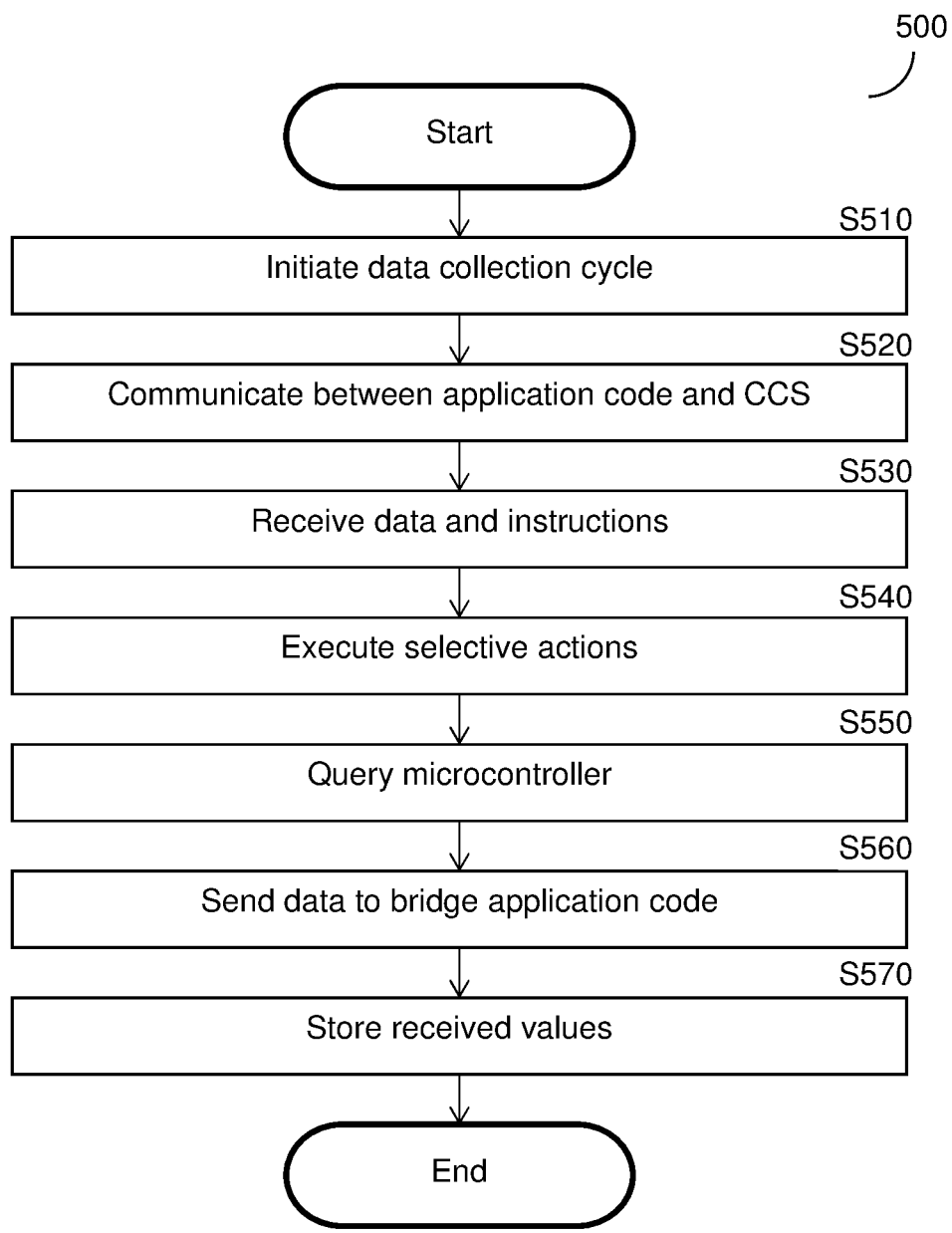
FIG. 5 is a flowchart depicting a first phase of a method for collecting data from one or more local devices, according to an embodiment.

FIG. 5 is an example flowchart 500 depicting a first phase of a method for collecting data from one or more local devices, according to an embodiment. It should be understood that the various aspects of the method described with respect to the flowchart 500 may be executed by a bridge device, such as the bridge device, 130, of FIG. 1, above.

At S510, a data collection cycle is initiated. A data collection cycle is a process for collecting data from one or more local device including, without limitation, the bridge devices. A data collection cycle may be initiated by application code, which may reside or run in an application layer included in a SBC, or the apparatus.

Further, at S510, if bridge device custom code is configured, the beforeCCSQuery method may be invoked after the execution of S510 and before the execution of S520. The beforeCCSQuery may be a custom-defined method configured to provide for execution of one or more user-specified processes before the execution of S520.

At S520, application code communicates with the CCS. The communicating application code, as described hereinabove, may run or reside in an application layer included, as described in a bridge device. The application code may be configured to communicate with the CCS via, without limitation, a network. Further, the application code may be configured to communicate with the CCS via one or more protocols including, without limitation, Hypertext Transfer Protocol Secure (HTTPS), and the like. The application code may be configured to communicate with the CCS at S520 for purposes including, without limitation, initiating data transfer processes, transferring data between the CCS and the application code, other, like, purposes, and any combination thereof.

At S530, data and instructions are received. Data and instructions include one or more data features relevant to purposes including, without limitation, providing updates to bridge and sensor devices, collecting data from bridge and sensor devices, and the like, as well as any combination thereof. Data and instructions may be received by application code residing or running in a bridge device, as described hereinabove, from a CCS, such as is described herein. Receiving data and instructions at S530 may include determining, by a CCS, which data and instructions are relevant to the bridge device, from which communication is executed at S520. Determining which data and instructions are relevant to the bridge device may include determination of the communicating bridge device's serial number, determination of sensor devices associated with the communicating bridge device, including such a determination based on the contents of one or more configuration databases, such as may be included in a CCS, other, like, determinations, and any combination thereof.

At S540, selective actions are executed. Selective actions are actions specified in one or more instructions received from the CCS at S530. Selective actions may include instructions specifying the initiation of device updates, the initiation of device data collection, other, like, instructions, and any combination thereof. In an example, where the data and instructions received at S530 include only instructions specifying routine data collection, S540 may include the execution only of routine data collection instructions.

At S540, if bridge device custom code is configured, the afterCCSQuery method may be invoked after the execution of S540 and before the execution of S550. Further, if bridge device custom code is configured, the beforeWBRRegisters method may be invoked after the execution of S540 and before the execution of S550. It may be understood that, where the afterCCSQuery and beforeWBRRegisters methods are both invoked after the execution of S540 and before the execution of S550, the methods may be invoked in any order, including simultaneously, without loss of generality or departure from the scope of the disclosure. AfterCCSQuery and beforeWBRRegisters may be custom-defined methods providing for the execution of one or more user-specified processes before the execution of S550. Further, it may be understood that, in addition to, or instead of, the afterCCSQuery and beforeWBRRegisters method, other, like, methods may be invoked at S540. Methods which may be invoked at S540 include, without limitation, methods providing for various updates, enhancements, changes, and the like, including via over-the-air (OTA) communication, other, like, methods, and any combination thereof.

At S550, a microcontroller of the bride device is queried. The microcontroller may be queried by application code residing or running in an application layer, such as is described herein, for purposes including, without limitation, collecting one or more bridge or sensor device data features including, without limitation, sensor data, device state descriptions, various registers pertaining to device operation, and the like, as well as any combination thereof. Querying of the microcontroller at S550 may be further executed for other purposes like those described herein, as well as any combination of those like purposes and those described herein. The bridge device main CPU may be queried by one or more means including, without limitation, SPI connections, and the like, as well as any combination thereof.

At S560, data is sent to bridge application code. Data may be sent to bridge application code, as described herein, by program binary code, where program binary code may be included in program memory, such as the program memory, 275, of FIG. 2b, above, and where such program memory may be further included in a microcontroller, such as the microcontroller, 260, of FIG. 2b, above. Further, at S560, the program binary code may be configured to execute or respond to one or more features of the bridge device main CPU query of S550, providing relevant data, including data responsive to the described query or queries, to the application code, described herein, via one or more means including, without limitation, SPI communications, and the like, as well as any combination thereof.

At S570, received values are stored. Received values include those data features sent to bridge application code at S560. Received values may be stored to one or more memory or storage components including, without limitation a most recent values database, such as the most recent values database, 331, of FIG. 3, above, other, like, databases, and any combination thereof.

If, at S570, bridge device custom code is configured, the afterWBRRegisters method may be invoked after the execution of S570, the afterWBRRegisters method may be a custom-defined method providing for the execution of one or more user-specified processes after the execution of S570.

Figure 6:
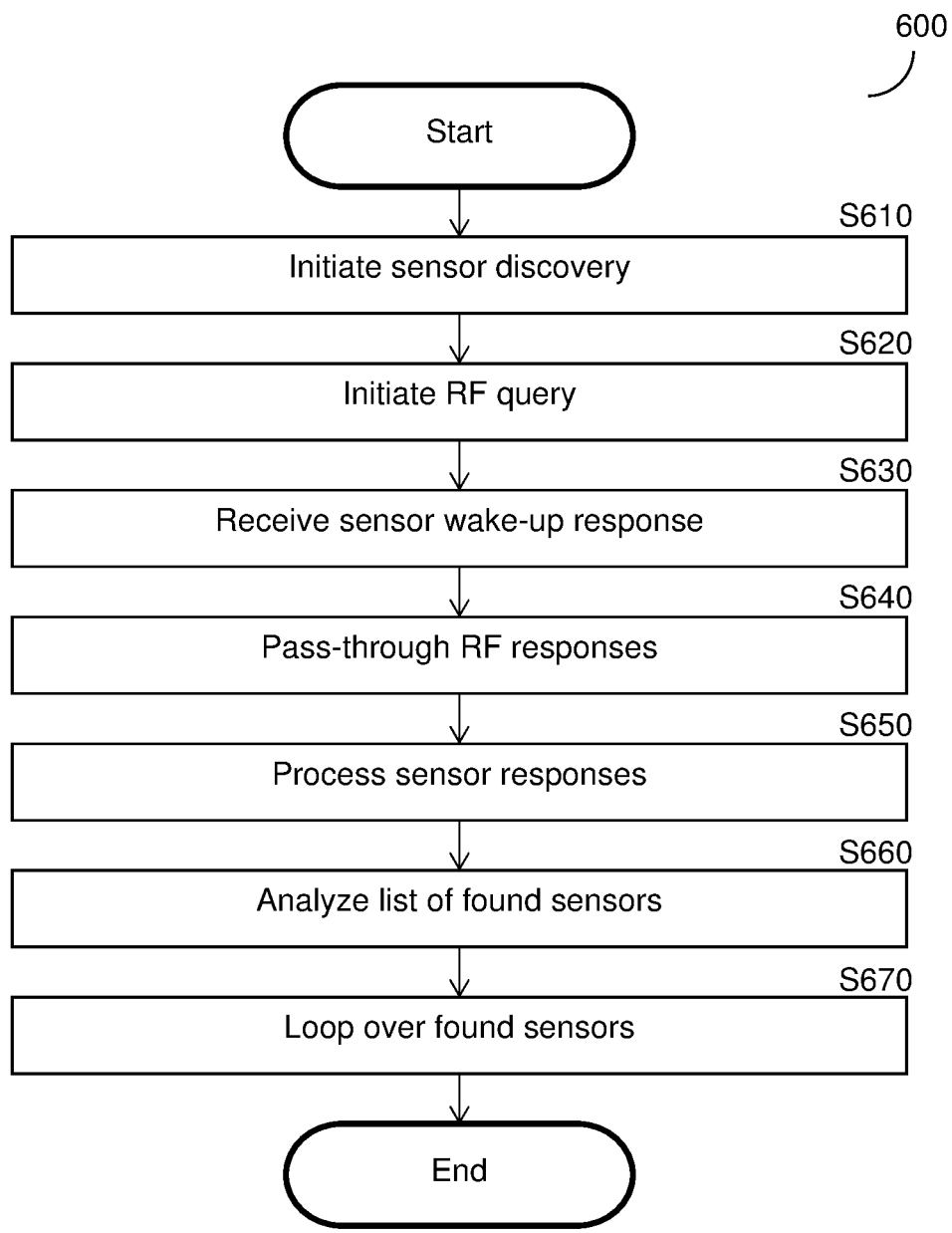
FIG. 6 is a flowchart depicting a second phase of a method for collecting data from one or more local devices, according to an embodiment.

FIG. 6 is an example flowchart 600 depicting a second phase of a method for collecting data from one or more local devices, according to an embodiment. It should be understood that the various aspects of the method described with respect to the flowchart 600 may be executed by a bridge device, such as the bridge device, 130, of FIG. 1, above, as well as the various components and sub-components thereof, unless otherwise specified.

At S610, sensor discovery is initiated. Sensor discovery, as initiated at S610, is a process for polling, locating, and mapping on-line sensor devices. Sensor devices, as described hereinabove, may include various sensors, other, like, devices, and any combination. Sensor discovery may, in an embodiment, include discovery only of sensors including data for collection. Sensor discovery, at S610, may be initiated by the issuance of one or more commands to bridge device binary code, as described hereinabove, by the bridge device application code, as also described hereinabove, by one or more means including, without limitation, via SPI connections, and the like, as well as any combination thereof.

At S620, RF querying is initiated. RF querying is a process for querying online sensor devices. RF querying may include generation and transmission of one or more querying signals. Querying signals may be radio-frequency (RF) signals broadcast to all sensor devices within range of the broadcasting device. Querying signals may include signals broadcast at one or more frequencies within the RF band. Further, querying signals may be encrypted, unencrypted, or encrypted to various degrees, including by application of one or more selective encryption parameters. RF querying may be initiated by the bridge binary code, as described hereinabove, with the transmission of signals provided by one or more components of the bridge device, such as the radio, 220, of FIG. 2a, above, and the like, as well as any combination thereof. In an embodiment, RF querying at S620 may include periodic transmission of one or more wake-up signals to each of the plurality of sensor devices. According to the same embodiment, a wake-up signal may include, without limitation, a synchronized time slot, and the like, as well as any combination thereof. Further, according to the same embodiment, the one or more wake-up signals may be sent during a first time period.

At S630, a sensor wake-up response is received. A sensor wake-up response may be a response generated by binary code native to a sensor device, specifying that the generating sensor device is "awake" and has received the RF query initiated at S620. Sensor wake-up responses may be generated by each sensor's sensor device binary code, wherein a sensor device, and its included binary code, may be configured to send a wake-up response in reference to a pre-defined time-slot. Further, sensor device wake-up responses may be received during a second time period, during other, like, time periods, and any combination thereof. Sensor wake-up responses may be received by one or more components of the bridge device, including the radio, as described hereinabove, and the like, as well as any combination thereof.

At S640, RF responses are passed-through. RF responses, including the sensor wake-up responses received at S630, may be passed-through by bridge device binary code, as described hereinabove. A pass-through process may include queuing one or more RF responses for transmission. Further, a pass-through process may include transmitting one or more RF responses, and the various queues thereof, to one or more components or sub-components of a bridge device including, without limitation, the application code described hereinabove, and the like, as well as any combination thereof.

At S650, sensor responses are processed. Sensor responses, as passed-through at S650, may be processed by bridge device application code, as described hereinabove. Processing sensor responses at S650 may include processing individual responses from each sensor. Further, processing sensor responses at S650 may include building one or more lists of available sensors. Lists of available sensors may be sorted, ranked, or otherwise organized based on a variety of factors including, without limitation, sensor identifiers, order of receipt, sensor types, sensor locations, and the like, as well as any combination thereof.

At S660, lists of found sensors are analyzed. Found sensor lists analyzed at S660 include those lists passed-through at S640 and processed at S650. Analysis of found sensor lists may include identification of one or more sensor devices matching selected sensor device identifiers, locations, types, and the like, as well as any combination thereof. Further, analysis of found sensor lists may include statistical analysis of one or more lists, including counts of sensor devices within each list, generation of trends, maps, and other, like, data features reflecting the contents of the various lists, other, like, analyses, and any combination thereof. In addition, analysis of found sensor lists may include execution of one or more necessary housekeeping tasks based on the list or lists analyzed. Necessary housekeeping tasks may include, as examples and without limitation, isolation of anomalous data, removal of redundant data, identification of mis-calibrated sensor devices, other, like, housekeeping tasks, and any combination thereof.

At S670, a looping process is executed over found sensors. A looping process is a repeating process for collecting one or more data features from the various sensor devices described herein. The execution of a looping process is described with respect to FIG. 7, below.

Figure 7:
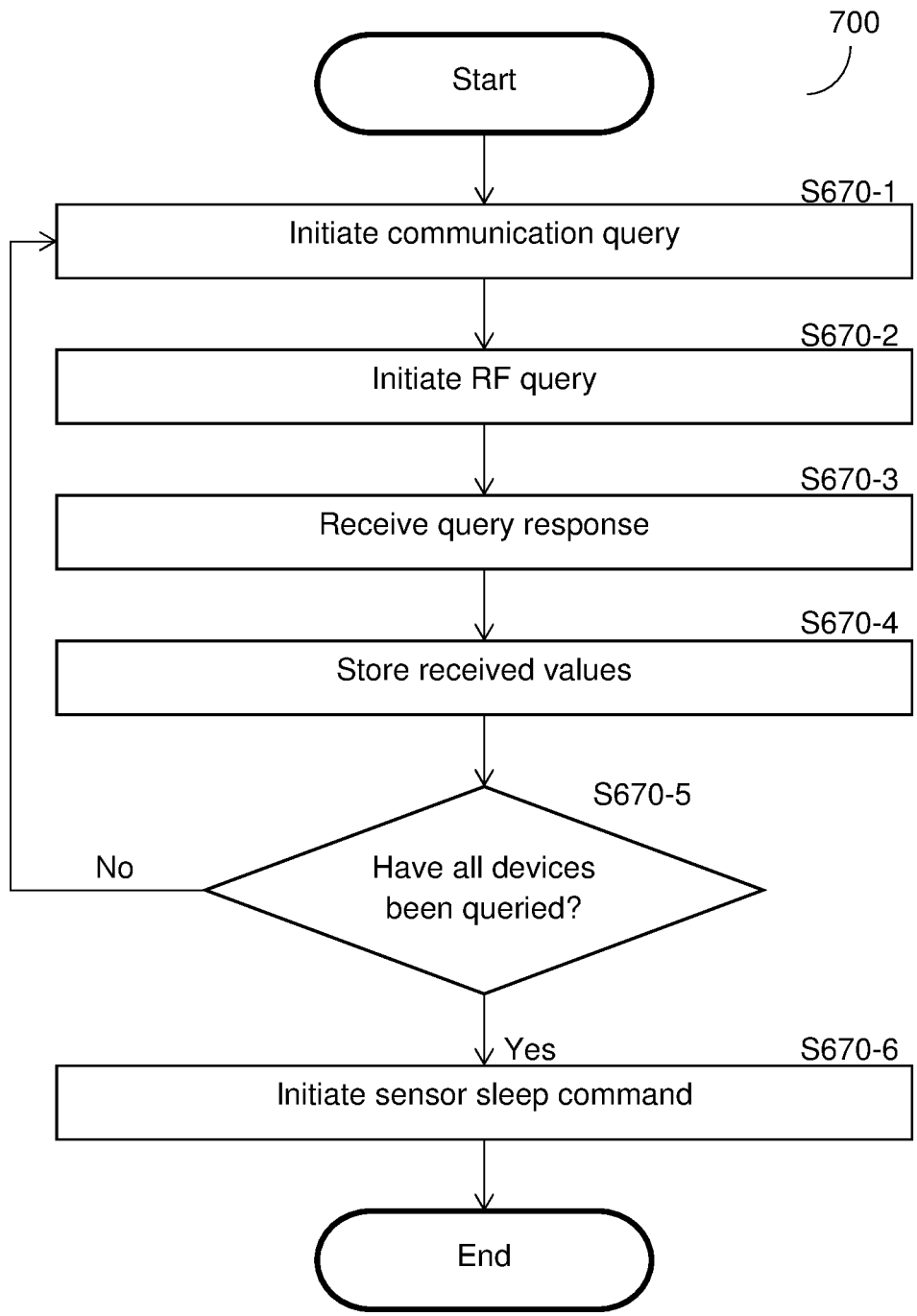
FIG. 7 is a flowchart depicting a looped method for collecting data from one or more local devices, as may be included in a second phase of a process for collecting data from one or more local devices, according to an embodiment.

FIG. 7 is an example flowchart 700 depicting a looped method for collecting data from one or more local devices, as may be included in a second phase of a process for collecting data from one or more local devices, according to an embodiment. It should be understood that the various aspects of the method described with respect to the flowchart 600 may be executed by a bridge device, such as the bridge device, 130, of FIG. 1, above, as well as the various components and sub-components thereof, unless otherwise specified.

At S670-1, communication querying is initiated. Communication querying is the transmission of one or more queries from bridge application code, as described herein, to one or more sensor devices. Communication querying may include directed querying, where a query is generated and transmitted to a specific sensor device based on the device's unique 32-bit address. Queries may include one or more instructions, commands, methods, data features, and the like, including, without limitation, "GetRegisters" instructions, which may configure one or more sensor devices to return one or more registers, "GetStatistics" instructions which may configure one or more sensor devices to return one or more operation or data statistics, and the like, as well as any combination thereof.

At S670-2, RF querying is initiated. Radio-Frequency (RF) querying, as described with respect to S620 of FIG. 5, above, is a process for querying online sensor devices. RF querying at S670-2 may include querying of one or more sensor devices, based on device addresses specified in the execution of S670-1. RF querying at S670-2 may include, without limitation, collecting, from each found sensor device, at least one sensor device reading, and the like, as well as any combination thereof. Further sensor device readings may include at least an air quality level in the vicinity of the one or more sensor devices. As at S620 of FIG. 5, above, RF querying may be executed by bridge device binary code, as described hereinabove, and RF queries may be transmitted to one or more sensor devices by various means including, without limitation, via the radio, 220, of FIG. 2a, above.

At S670-3, query responses are received. Query responses are generated by the one or more sensor devices to which RF queries are dispatched at S670-2. Query responses may include data responsive to one or more instructions or commands included in the queries described with respect to S670-1, above. Query receiving, and generation and dispatch of query responses may be executed by sensor binary code, such as is described herein. Query responses may be sent by the respective sensor devices, including at predefined time intervals, where such time intervals may be specified in the query described hereinabove, in various features of bridge or sensor device configuration, and the like, as well as any combination thereof. Sensor query responses may be received, at S670-3, by the bridge binary code described hereinabove.

At S670-4, received values are stored. Received values may be stored by the bridge application layer, as described herein, to one or more storage or memory components including, without limitation, the most recent values database, 331, of FIG. 3, below, and the like, as well as any combination thereof.

At S670-5, it is determined whether all sensor devices have been queried.

Determination of whether all devices have been queried may include comparison of query responses received with one or more lists of connected sensor devices, such those lists analyzed at S660 of FIG. 5, above. Where, at S670-5, it is determined that all devices have been queried, execution continues with S670-6. Where, at S670-5, it is determined that all devices have not been queried, execution continues with S670-1.

At S670-6, a sensor sleep command is initiated. A sensor sleep command is an instruction providing for configuration of one or more connected sensor devices into a low-power state. A sensor sleep command may be issued in a manner similar or identical to that described with respect to transmission of queries at S670-1. Further, a sensor sleep command may be issued during a fourth time period, during other, like, time periods, and the like, as well as any combination thereof. A sensor sleep command may be initiated by bridge device application code, as described hereinabove, and may be issued via those various hardware components configured to provide for communication between a bridge device and the various sensor devices connected thereto.

Figure 8:
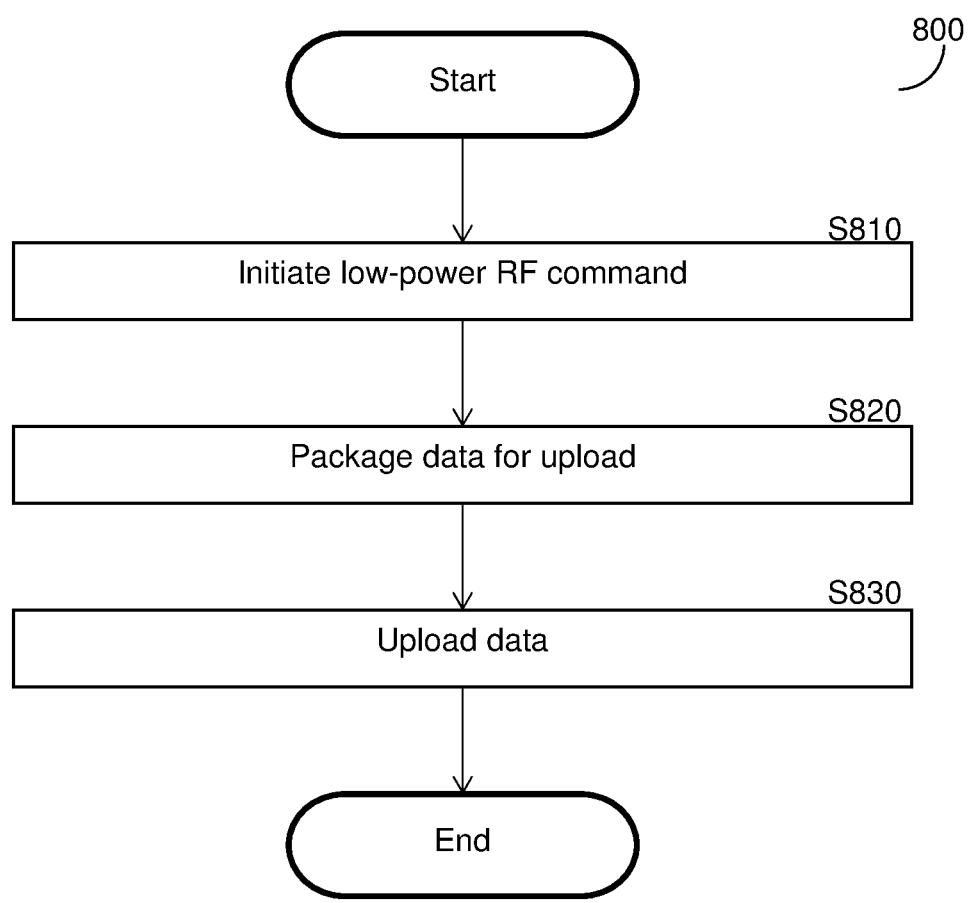
FIG. 8 is a flowchart depicting a third phase of a method for collecting data from one or more local devices, according to an embodiment.

FIG. 8 is an example flowchart 800 depicting a third phase of a method for collecting data from one or more local devices, according to an embodiment. It should be understood that the various aspects of the method described with respect to the flowchart 800 may be executed by a bridge device, such as the bridge device, 130, of FIG. 1.

At S810, a low-power RF command is initiated. A low-power RF command is an instruction providing for configuration of one or more sensor devices into a low-power state. A low-power RF command may be similar or identical to the sensor sleep command initiated with respect to S670-6 of FIG. 7, above. A low-power RF command may be initiated by one or more elements of a bridge device including, without limitation, bridge device binary code, as described hereinabove.

At S820, data is packaged for upload. Data packaged for upload at S820 may include one or more data features such as registers, and the like, including data collected during the execution of the various methods described herein, including the looped data collection method described with respect to FIG. 7, above. Data may be packaged for upload by one or more elements of a bridge device, including application code, as described herein, and the like, as well as any combination thereof. Packaging data for upload may include organization of relevant data, conversion of one or more data features into various other data types, such as registers, strings, comma-separated values (CSV), and the like, as well as any combination thereof, as well as other, like, data packaging operations and various combinations thereof. In addition, packaging data for upload at S820 may include encapsulating some or all relevant data, including, without limitation, sensor readings, registers, other, like, data features, and any combination thereof, into one or more data frames. Further, packaging data for upload may include queueing data to one or more storage or memory components including, without limitation, an SD card included in a bridge device, such as the SD card described hereinabove. Queueing of data at S820 may provide for data retention in the event that one or more target DUSs are unreachable or unavailable. Queueing of data at S820 may further provide for retention of collected data, preventing data loss, up to the limits of the queueing device's storage capacity, the storage capacities of other, connected devices, and the like, as well as any combination thereof. In addition packaging data for upload may include one or more attempts to upload packaged data to one or more data upload servers (DUSs), where a DUS may be the DUS, 115, of FIG. 1, above, via methods including, without limitation, connection between the bridge device and the DUS via the network, 120, of FIG. 1, above.

At S830, data is uploaded to one or more DUSs. Where data is uploaded to one or more DUSs, the target DUSs may parse the uploaded data. Parsing of uploaded data by a DUS may include storing some or all of the uploaded data in a time-series database. Further, parsing of uploaded data by a DUS may include storing some or all register values, included in the uploaded data, to a most recent values database. In an embodiment S830 may include uploading of one or more data frames, as described with respect to S820, to a building management system (BMS), or component or sub-component thereof.

Figure 9:
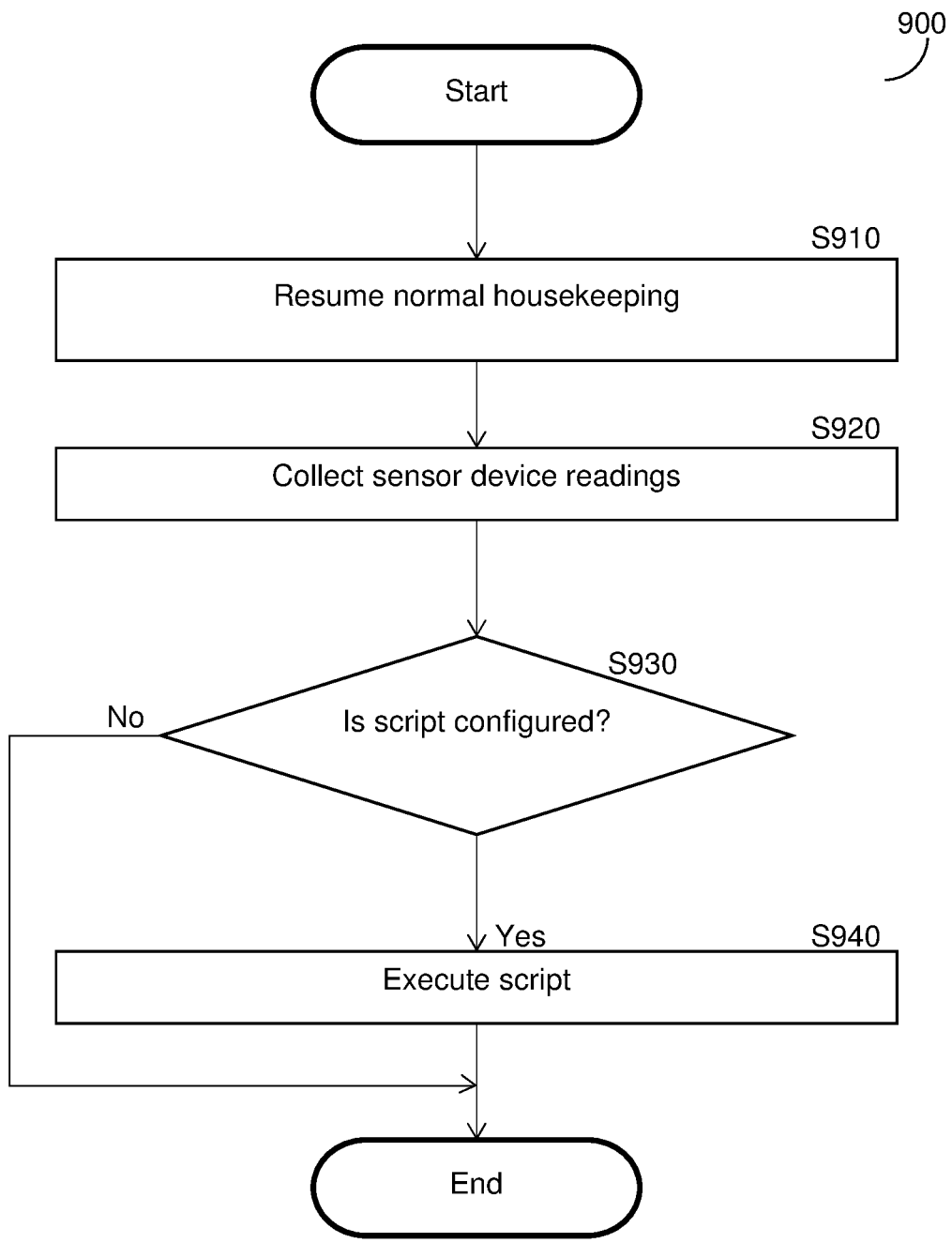
FIG. 9 is a flowchart depicting a method for collecting data from one or more local devices outside of inter-device communications, according to an embodiment.

FIG. 9 is an example flowchart 900 depicting a method for collecting data from one or more local devices outside of inter-device communications, according to an embodiment. It should be understood that the various aspects of the method described with respect to the flowchart 900 may be executed by a bridge device, such as the bridge device, 130, of FIG. 1, above, as well as the various components and sub-components thereof, unless otherwise specified.

At S910, normal housekeeping is resumed. Housekeeping may include one or more processes providing for maintenance, upkeep, and the like, of one or more aspects of a bridge device and the various connected sensor devices. Housekeeping may include, as examples and without limitation, removing redundant data features or registers, identifying anomalous data features or registers, isolating miscalibrated sensor devices, periodic reading of sensor values, and the like, as well as any combination thereof. Resumption of normal housekeeping activities at S910 may be executed by bridge device binary code, as described hereinabove. Resumption of normal housekeeping at S910 may further include similar resumption of one or more normal housekeeping activities by binary code included in one or more sensor devices.

At S920, sensor device readings are collected. Collecting sensor device readings, such as from the sensor devices, 140, of FIG. 1, above, may include collecting one or more data features from various sensor devices. Data features collected at S920, during the collection of sensor device readings, may include instantaneous sensor data, such as present-moment air quality readings, past, stored, sensor data, and the like, as well as any combination thereof. Collection of sensor device readings at S920 may be executed by bridge device binary code, as described hereinabove. Further, collection of sensor device readings at S920 may further include collection of sensor device readings by binary code included in the respective sensor devices.

At S930, it is determined whether, a script is configured. A script may be a script, command, instruction, or other, like, data feature, configured to provide for operation or modification of one or more aspects of the operation of bridge devices, sensor devices, or both. The scripts may be user-generated, pre-defined, or any combination thereof. Determination at S930 may be undertaken by bridge device binary code, sensor device binary code, or both, including simultaneously.

Where, at S930, it is determined that a script is configured, execution continues with S940. Where, at S930, it is determined that a script is not configured, execution terminates.

At S940, a script is executed. As described hereinabove, a script may be a script, command, instruction, or the like. Further, a script, as may be executed at S940, may provide for the manipulation of one or more data registers, such as those collected as described hereinabove. Execution of scripts at S940 may include execution by bridge device binary code, sensor device binary code, or both, including simultaneously.

Figure 10:
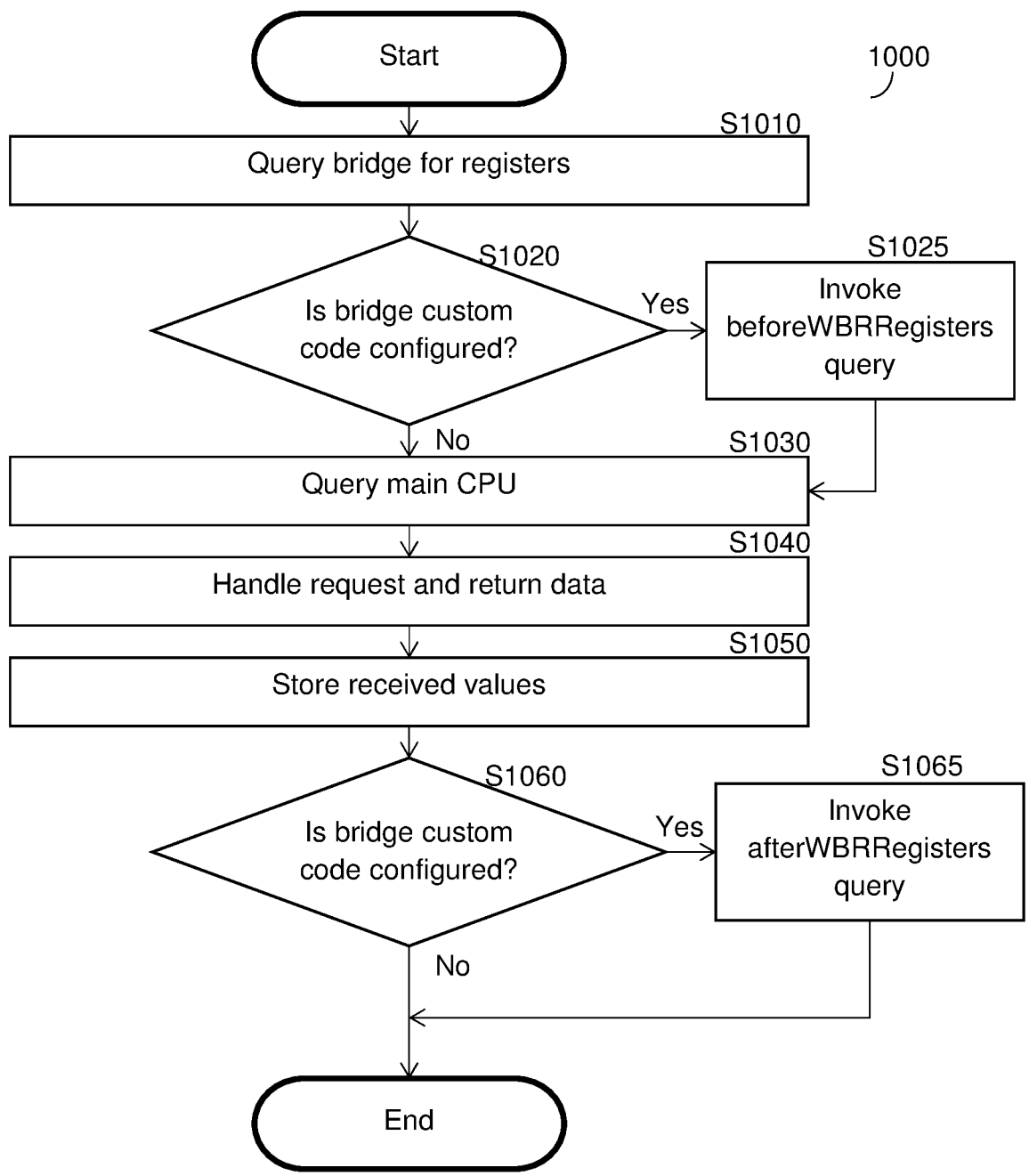
FIG. 10 is a flowchart depicting a method for application code register exchanges, according to an embodiment.

FIG. 10 is an example flowchart 1000 depicting a method for application code register exchanges, according to an embodiment. It should be understood that the various aspects of the method described with respect to the flowchart 1000 may be executed by a bridge device, such as the bridge device, 130, of FIG. 1, above, as well as the various components and sub-components thereof, unless otherwise specified.

At S1010, the bridge device is queried for registers. The bridge device may be queried for registers by application code included in the bridge device, as described hereinabove. Querying the bridge device for registers at S1010 may include generation and execution of one or more commands, instructions, and the like, configured to determine whether registers are included in one or more memory or storage components of the bridge device. Querying the bridge device may further include generation of one or more queries specific to various register types, source devices, receipt conditions, such as time, order, and the like, as well as other, like, queries, and any combination thereof. S1010 may be executed on various time-dependent intervals such as, as an example and without limitation, on a one-minute interval between five-minute cycles, where such five-minute cycles may be the various housekeeping and data collection cycles described hereinabove.

At S1020, it is determined whether bridge custom code is configured. Where, at S1020, it is determined that bridge custom code is configured, execution continues with S1025. Where, at S1020, it is determined that bridge custom code is not configured, execution continues with S1030.

At S1025, the beforeWBRRegisters method is invoked. The beforeWBRRegisters method may be a custom-defined method configured to provide for execution of one or more user-specified processes before the execution of S1030.

At S1030, the bridge device's microcontroller is queried. The microcontroller may be queried by application code included in the bridge device, as described herein. A query executed at S1030 may include, without limitation, query elements directed to the determination of the existence and location, as well as the collection, of one or more registers. A query executed at S1030 may be directed to user registers, providing support for integration with various building management systems (BMSs). The bridge device's main CPU may be queried at S1030 via one or more means including, without limitation, by SPI connections, as described herein, and the like, as well as any combination thereof.

At S1040, the request is handled, and data is returned. The request, which may include the one or more queries generated and sent at S1030, may be handled by bridge device binary code, as described herein. Request handling may include identification and location of one or more data features, registers, and the like, matching those specified in the query or queries, as well as the return of such data features or registers. Data may be returned from bridge device binary code to bridge device application code by one or more means including, without limitation, via SPI connections, as discussed herein, and the like, as well as any combination thereof.

At S1050, received values are stored. Received values may include one or more data features, registers, and the like returned at S1040. Received values may be stored by bridge device application code to one or more memory or storage components of the bridge including, without limitation, the most recent values database.

At S1060, it is determined whether bridge custom code is configured. Where, at S1060, it is determined that bridge custom code is configured, execution continues with S1065. Where, at S1060, it is determined that bridge custom code is not configured, execution terminates.

At S1065, the afterWBRRegisters method is invoked. The afterWBRRegisters method may be a custom-defined method configured to provide for execution of one or more user-specified processes after the execution of S1060.

Figure 11:
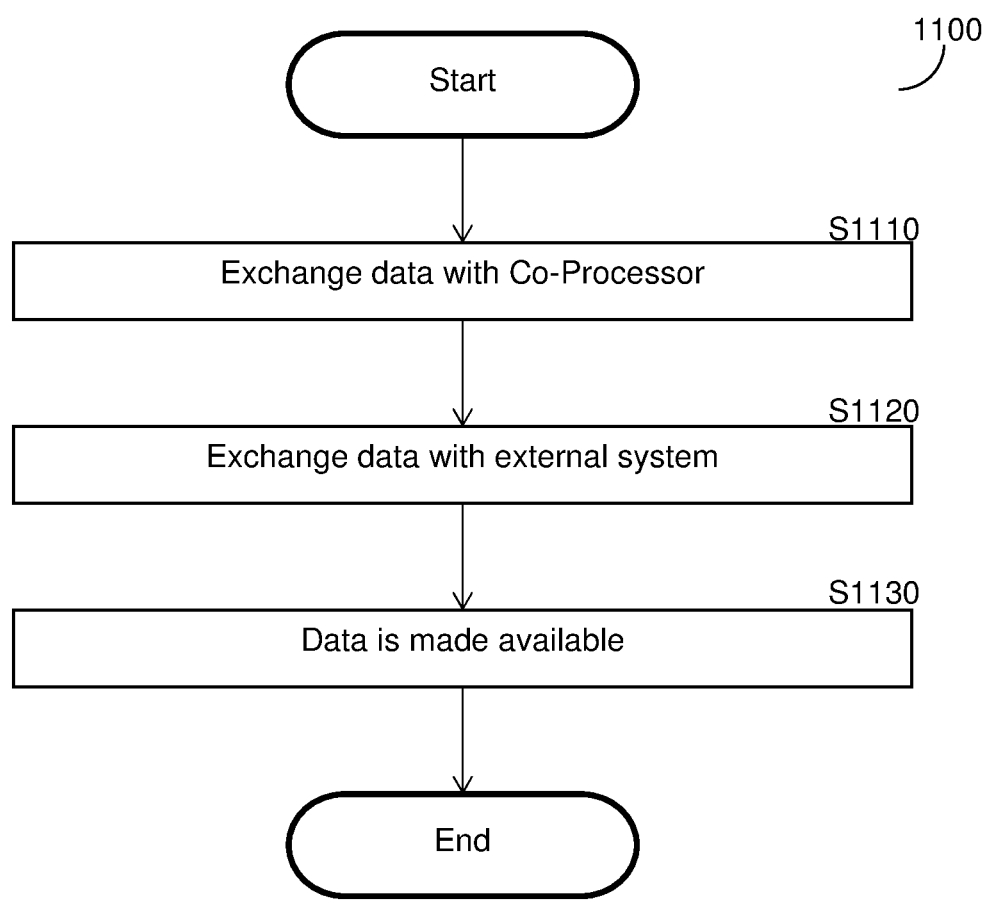
FIG. 11 is a flowchart depicting a method for task execution by a co-processor, according to an embodiment.

FIG. 11 is an example flowchart 1100 depicting a method for task execution by a co-processor, according to an embodiment.

At S1110, data is exchanged with a Co-Processor. Data exchanges with a Co-Processor may include exchanges implemented during regular loop code execution, such as the execution of the looping process described with respect to FIG. 7, above. Exchanging data may include exchanging one or more data registers, elements, features, and the like, including, without limitation, collected registers, device updates, and the like, as well as any combination thereof. Further, data exchanges at S1110 may include exchanges between bridge device binary code and a Co-Processor, exchanges between sensor device binary code and a Co-Processor, and the like. Exchanges executed at S1110 may be conducted via one or more means including, without limitation, via SPI connections, and the like, as well as any combination thereof.

At S1120, data is exchanged with an external system. Exchanges of data with external systems may be initiated by one or more components of a bridge device including, without limitation, a Co-Processor, as described herein, and the like, as well as any combination thereof. Exchanges of data with external systems at S1120 may include exchanges with one or more building management system (BMS) systems, devices, and the like. Exchanges at S1120 may be executed at task-specific intervals, where task-specific intervals may be various pre-set or user-defined time periods specific to various bridge and sensor operations. Examples of task-specific intervals may include a first time-period specific to a data collection task, a second time-period specific to a device update push task, and the like, as well as any combination thereof. Further, data exchanges executed at S1020 may include exchanges between external systems and bridge device Co-Processors, exchanges between external systems and sensor device Co-Processors, and the like. Data exchanges executed at S1120 may be conducted via one or more protocols including, without limitation, RS-type serial protocols, as described hereinabove, such as BACNet MSTP and Modbus RTU, and the like, as well as any combination thereof.

In an embodiment, exchanges of data with an external system at S1120 may include exchange configurations wherein a bridge device, or component or sub-component thereof, executing an exchange of data at S1120, is configured to serve as a "master" device, providing scheduling, configuration, and other, like, administration of data exchanges with one or more external systems. In an additional embodiment, a bridge device, or component or sub-component thereof, executing an exchange of data at S1120, is configured to serve as a "slave" device, receiving commands or instructions, from an external system, wherein the received commands or instructions initiate a process for reading data from the bridge device, writing data to the bridge device, or both. In a further embodiment, a bridge device may be configured to operate in one or more of the "master" or "slave" modes described previously, including simultaneously.

Further, in an embodiment, a bridge device, or component or sub-component thereof, executing an exchange of data with one or more external systems at S1120 may be configured to operate in "listener mode." Where a bridge device is configured to operate in "listener" mode at S1120, the bridge device may be configured to log data passing through a communications bus for purposes including, without limitation, diagnostic analysis of logged traffic, and the like, as well as any combination thereof.

At S1130, data is made available by one or more elements of the various bridge and sensor devices including, without limitation, bridge device binary code, sensor device binary code, and the like. Where data is made available by bridge device binary code, data may be made available for transmission to various elements of a bridge device, including bridge device application code layers, as described herein, as well as for transmission to other, like, devices and components thereof, as well as any combination thereof. Further, where data is made available by sensor device binary code, data may be made available for transmission to one or more components of a bridge device upon receipt of an RF request, as described hereinabove.

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other sensor units may be connected to the computer platform such as an additional data storage unit and a printing unit. Furthermore, a non-transitory computer readable medium is any computer readable medium except for a transitory propagating signal.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

What is claimed is:

1. A bridge device operable in an air-quality control system, the bridge device is connected to a plurality of sensor devices, the bridge device comprising:
a radio circuit configured to wirelessly communicate with the plurality of sensor devices over a wireless medium using an air-quality communication protocol;
a transceiver configured to communicate with a remote server;
a processing circuitry;
a memory, the memory containing instructions that, when executed by the processing circuitry, configure the bridge device to:
periodically discover the plurality of sensor devices connected to the bridge device;
query each of the discovered senor devices to read at least one senor reading provided by each sensor device, wherein the at least one senor reading is of at least an air-quality level in a vicinity of the sensor device;
encapsulate the sensor readings from the plurality of sensor devices into a data frame; and
send the data frame to the remote server;
wherein the bridge device is Characterized by being further configured to:
periodically send wake-up signals to each of the plurality of sensor devices, wherein the wake-up signal includes at least a packet number, wherein the wake-up signals are sent during a first time period;
receive, during a second time period, from sensor devices, acknowledgment (ACK) signals during a second time period, wherein each sensor device is configured to send an ACK signal in reference to a synchronized time slot and the packet number;
query, during a third time period, each sensor device sending a woke-up signal to gather its respective at least one sensor reading; and
send, during a fourth time period, sleep signals to the plurality of sensor devices.

2. The bridge device of claim 1, wherein the bridge device is further configured to:
asynchronously command the plurality of sensor devices.

3. The bridge device of claim 1, wherein the bridge device is further configured to:
asynchronously command the plurality of sensor devices in response to instructions received from the remote server.

4. The bridge device of claim 1, wherein the wireless medium includes at least the industrial, scientific and medical (ISM) frequency bands.

5. The bridge device of claim 1, wherein the bridge device is further configured to communicate with a command and control server, wherein the command and control server controls the bridge device and interfaces with the remote server.

6. The bridge device of claim 1, wherein the memory includes a secured code repository including instructions for activating the bridge device, activating collection of sensor readings, and activating collection of the data from the bridge device.

7. The bridge device of claim 1, wherein the processing circuitry further includes:
a main processor configured to control the operation of the bridge device;
a co-processor configured to process instructions received from at least the remote server; and
a microcontroller configured to configure code update of the bridge device and the plurality of sensor devices over the air.

8. The bridge device of claim 1, wherein the bridge device is configured with a unique serial number providing a persistent encoding of attributes of the bridge device.

9. The bridge device of claim 1, wherein the communication between the remote server is performed by implementing any one of: an RS-based protocol and an Ethernet based protocol.

10. The bridge device of claim 1, wherein each of the plurality of sensors includes at least one of: at least one gas detector, at least one measurement sensor, and at least one building system actuator.

11. The bridge device of claim 1, wherein the bridge device further comprises:
a touch screen display configured to display settings of the bridge devices and collected sensor readings.

12. The bridge device of claim 1, wherein the at least one sensor readings include any one of: instantaneous sensor readings and past stored sensor readings.

13. The bridge device of claim 2, wherein a command includes a self-calibration of a sensor device.

14. The bridge device of claim 1, wherein the air-quality communication protocol allows for maximization of a distance between the bridge device and the plurality of sensor devices, while minimizing power consumption by each of the plurality of sensor devices.

15. The bridge device of claim 1, wherein the remote server is deployed in a cloud computing platform and the bridge device is deployed on-premises.

16. The bridge device of claim 1, wherein the remote server and the bridge device are deployed on-premises.

17. The bridge device of claim 1, where the data frame is encrypted using one of a plurality of encryption keys stored in the memory.

18. The bridge device of claim 1, wherein the bridge device includes at least one measurement sensor.

19. A method for operating a bridge device, wherein the bridge device is connected to a plurality of sensor devices in an air-quality control system, comprising:
periodically discovering the plurality of sensor devices connected to the bridge device;

querying each of the discovered senor devices to read at least one sensor reading provided by each sensor device, wherein the at least one sensor reading is of at least an air-quality level in a vicinity of the sensor device;

encapsulating the sensor readings from the plurality of sensor devices into a data frame; and sending the data frame to a remote server;

the method being Characterized by:

periodically sending wake-up signals to each of the plurality of sensor devices, wherein the wake-up signal includes at least a packet number, wherein the wake-up signals are sent during a first time period;

receiving, during a second time period, from sensor devices, acknowledgement (ACK) signals during a second time period, wherein each sensor device is configured to send an ACK signal in reference to a synchronized time slot and a packet number;

querying, during a third time period, each sensor device sending a woke-up signal to gather its respective at least one sensor reading; and sending, during a fourth time period, sleep signals to the plurality of sensor devices.

20. The method of claim 19, wherein the bridge device communicates with the plurality of sensor devices over a wireless medium.

21. The method of claim 19, further comprising:

encrypting the data frame using one of a plurality of encryption keys stored in a memory of the bridge device.

* * * * *